(12) United States Patent
Conlon

(10) Patent No.: US 11,937,839 B2
(45) Date of Patent: Mar. 26, 2024

(54) CATHETER WITH ELECTRICALLY ACTUATED EXPANDABLE MOUTH

(71) Applicant: Neuravi Limited, Galway (IE)

(72) Inventor: Richard Conlon, Naas (IE)

(73) Assignee: NEURAVI LIMITED, Galway (IE)

( * ) Notice: Subject to any disclaimer, the term of this patent is extended or adjusted under 35 U.S.C. 154(b) by 164 days.

(21) Appl. No.: 17/487,060

(22) Filed: Sep. 28, 2021

(65) Prior Publication Data

US 2023/0116901 A1    Apr. 13, 2023

(51) Int. Cl.
| | | |
|---|---|---|
| A61B 17/221 | (2006.01) | |
| A61M 25/00 | (2006.01) | |
| A61M 25/01 | (2006.01) | |
| A61B 17/00 | (2006.01) | |
| A61B 17/22 | (2006.01) | |

(52) U.S. Cl.
CPC ....... *A61B 17/221* (2013.01); *A61M 25/0074* (2013.01); *A61M 25/0108* (2013.01); *A61B 2017/00017* (2013.01); *A61B 2017/00526* (2013.01); *A61B 2017/00862* (2013.01); *A61B 2017/22079* (2013.01); *A61B 2017/2215* (2013.01); *A61M 2205/0216* (2013.01); *A61M 2205/0233* (2013.01); *A61M 2207/00* (2013.01)

(58) Field of Classification Search
CPC .............. A61M 25/0074; A61M 29/00; A61B 2017/00017; A61B 2017/22079; A61B 2017/2215; A61B 17/22031
See application file for complete search history.

(56) References Cited

U.S. PATENT DOCUMENTS

| | | |
|---|---|---|
| 4,243,040 A | 1/1981 | Beecher |
| 4,324,262 A | 4/1982 | Hall |
| 4,351,342 A | 9/1982 | Wiita et al. |

(Continued)

FOREIGN PATENT DOCUMENTS

| | | |
|---|---|---|
| AU | 2015271876 B2 | 9/2017 |
| CN | 1658920 A | 8/2005 |

(Continued)

OTHER PUBLICATIONS

US 6,348,062 B1, 02/2002, Hopkins (withdrawn)

(Continued)

*Primary Examiner* — Sarah A Long
(74) *Attorney, Agent, or Firm* — TROUTMAN PEPPER HAMILTON SANDERS LLP

(57) ABSTRACT

Devices described herein include an actuated clot retrieval catheter system. The system includes a catheter having a metallic region positioned at the distal tip of the catheter. The metallic region includes at least two abutting metals in a bimetallic coil configuration. The bimetallic coil expands to form a seal with the inner wall of a vessel. In some examples, the bimetallic coil also captures a clot for removal from the vessel. The bimetallic coil is manufactured from metal-based materials having different thermal expansion coefficients. Conductive wires extend along a longitudinal axis of the catheter from an electrical current controller to at least a portion of the metallic region. Electrical current to the metallic region causes the bimetallic coil to transition from a tight configuration to an expanded configuration and remove the clot.

16 Claims, 7 Drawing Sheets

(56) References Cited

U.S. PATENT DOCUMENTS

| | | |
|---|---|---|
| 4,575,371 A | 3/1986 | Nordqvist et al. |
| 4,592,356 A | 6/1986 | Gutierrez |
| 4,719,924 A | 1/1988 | Crittenden et al. |
| 4,738,666 A | 4/1988 | Fuqua |
| 4,767,404 A | 8/1988 | Renton |
| 4,793,348 A | 12/1988 | Palmaz |
| 4,873,978 A | 10/1989 | Ginsburg |
| 5,011,488 A | 4/1991 | Ginsburg |
| 5,092,839 A | 3/1992 | Kipperman |
| 5,102,415 A | 4/1992 | Guenther et al. |
| 5,122,136 A | 6/1992 | Guglielmi et al. |
| 5,123,840 A | 6/1992 | Nates |
| 5,171,233 A | 12/1992 | Amplatz |
| 5,234,437 A | 8/1993 | Sepetka |
| 5,256,144 A | 10/1993 | Kraus et al. |
| 5,261,916 A | 11/1993 | Engelson |
| 5,372,124 A | 12/1994 | Takayama et al. |
| 5,385,562 A | 1/1995 | Adams |
| 5,387,219 A | 2/1995 | Rappe |
| 5,387,226 A | 2/1995 | Miraki |
| 5,396,902 A | 3/1995 | Brennen et al. |
| 5,449,372 A | 9/1995 | Schmaltz |
| 5,520,651 A | 5/1996 | Sutcu |
| 5,538,512 A | 7/1996 | Zenzon et al. |
| 5,549,626 A | 8/1996 | Miller et al. |
| 5,558,652 A | 9/1996 | Henke |
| 5,601,600 A | 2/1997 | Ton |
| 5,609,627 A | 3/1997 | Goicoechea et al. |
| 5,624,461 A | 4/1997 | Mariant |
| 5,639,277 A | 6/1997 | Mariant |
| 5,645,558 A | 7/1997 | Horton |
| 5,658,296 A | 8/1997 | Bates |
| 5,662,671 A | 9/1997 | Barbut |
| 5,695,519 A | 12/1997 | Summer et al. |
| 5,709,704 A | 1/1998 | Nott et al. |
| 5,713,853 A | 2/1998 | Clark |
| 5,728,078 A | 3/1998 | Powers, Jr. |
| 5,769,871 A | 6/1998 | Mers Kelly |
| 5,779,716 A | 7/1998 | Cano |
| 5,810,874 A | 9/1998 | Lefebvre |
| 5,814,064 A | 9/1998 | Danniel et al. |
| 5,827,304 A | 10/1998 | Hart |
| 5,846,251 A | 12/1998 | Hart |
| 5,855,598 A | 1/1999 | Pinchuk |
| 5,893,869 A | 4/1999 | Barnhart et al. |
| 5,895,398 A | 4/1999 | Wensel |
| 5,897,567 A | 4/1999 | Ressemann |
| 5,904,698 A | 5/1999 | Thomas et al. |
| 5,911,725 A | 6/1999 | Boury |
| 5,935,139 A | 8/1999 | Bates |
| 5,938,645 A | 8/1999 | Gordon |
| 5,947,995 A | 9/1999 | Samuels |
| 5,968,057 A | 10/1999 | Taheri |
| 5,971,938 A | 10/1999 | Hart et al. |
| 5,997,939 A | 12/1999 | Moechnig et al. |
| 6,022,343 A | 2/2000 | Johnson et al. |
| 6,063,113 A | 5/2000 | Kavteladze |
| 6,066,149 A | 5/2000 | Samson et al. |
| 6,066,158 A | 5/2000 | Engelson |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates |
| 6,102,932 A | 8/2000 | Kurz |
| 6,106,548 A | 8/2000 | Roubin et al. |
| 6,129,739 A | 10/2000 | Khosravi |
| 6,142,957 A | 11/2000 | Diamond et al. |
| 6,146,396 A | 11/2000 | Konya et al. |
| 6,146,404 A | 11/2000 | Kim |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi |
| 6,203,561 B1 | 3/2001 | Ramee |
| 6,214,026 B1 | 4/2001 | Lepak |
| 6,221,006 B1 | 4/2001 | Dubrul |
| 6,238,412 B1 | 5/2001 | Dubrul |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,306,163 B1 | 10/2001 | Fitz |
| 6,309,379 B1 | 10/2001 | Willard |
| 6,312,407 B1 | 11/2001 | Zadno-Azizi et al. |
| 6,312,444 B1 | 11/2001 | Barbut |
| 6,315,778 B1 | 11/2001 | Gambale et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,348,056 B1 | 2/2002 | Bates |
| 6,350,271 B1 | 2/2002 | Kurz et al. |
| 6,361,545 B1 | 3/2002 | Macoviak |
| 6,371,963 B1 | 4/2002 | Nishtala et al. |
| 6,375,668 B1 | 4/2002 | Gifford et al. |
| 6,383,205 B1 | 5/2002 | Samson et al. |
| 6,383,206 B1 | 5/2002 | Gillick |
| 6,391,037 B1 | 5/2002 | Greenhalgh |
| 6,402,771 B1 | 6/2002 | Palmer |
| 6,409,683 B1 | 6/2002 | Fonseca et al. |
| 6,416,541 B2 | 7/2002 | Denardo |
| 6,425,909 B1 | 7/2002 | Dieck et al. |
| 6,432,122 B1 | 8/2002 | Gilson et al. |
| 6,436,112 B2 | 8/2002 | Wensel |
| 6,458,139 B1 | 10/2002 | Palmer |
| 6,346,116 B1 | 11/2002 | Brooks et al. |
| 6,485,497 B2 | 11/2002 | Wensel |
| 6,485,501 B1 | 11/2002 | Green |
| 6,485,502 B2 | 11/2002 | Don Michael |
| 6,511,492 B1 | 1/2003 | Rosenbluth |
| 6,517,551 B1 | 2/2003 | Driskill |
| 6,520,934 B1 | 2/2003 | Lee et al. |
| 6,520,951 B1 | 2/2003 | Carrillo, Jr. |
| 6,530,935 B2 | 3/2003 | Wensel |
| 6,530,939 B1 | 3/2003 | Hopkins |
| 6,540,768 B1 | 4/2003 | Diaz et al. |
| 6,544,279 B1 | 4/2003 | Hopkins |
| 6,551,341 B2 | 4/2003 | Boylan et al. |
| 6,551,342 B1 | 4/2003 | Shen et al. |
| 6,575,997 B1 | 6/2003 | Palmer et al. |
| 6,582,448 B1 | 6/2003 | Boyle |
| 6,585,756 B1 | 7/2003 | Strecker |
| 6,589,265 B1 | 7/2003 | Palmer et al. |
| 6,592,607 B1 | 7/2003 | Palmer et al. |
| 6,592,616 B1 | 7/2003 | Stack |
| 6,602,271 B2 | 8/2003 | Adams |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi |
| 6,632,241 B1 | 10/2003 | Hanoock et al. |
| 6,638,245 B2 | 10/2003 | Miller |
| 6,638,293 B1 | 10/2003 | Makower et al. |
| 6,641,590 B1 | 11/2003 | Palmer et al. |
| 6,652,555 B1 | 11/2003 | VanTassel et al. |
| 6,656,218 B1 | 12/2003 | Denardo et al. |
| 6,660,021 B1 | 12/2003 | Palmer et al. |
| 6,663,650 B2 | 12/2003 | Sepetka |
| 6,673,089 B1 | 1/2004 | Yassour et al. |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,702,782 B2 | 3/2004 | Miller |
| 6,712,834 B2 | 3/2004 | Yassour et al. |
| 6,726,701 B2 | 4/2004 | Gilson et al. |
| 6,730,104 B1 | 5/2004 | Sepetka |
| 6,726,703 B2 | 8/2004 | Broome et al. |
| 6,824,545 B2 | 11/2004 | Sepetka |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer |

(56) References Cited

U.S. PATENT DOCUMENTS

| | | |
|---|---|---|
| 6,913,618 B2 | 7/2005 | Denardo et al. |
| 6,953,472 B2 | 10/2005 | Palmer et al. |
| 6,989,019 B2 | 1/2006 | Mazzocchi |
| 6,989,021 B2 | 1/2006 | Bosma et al. |
| 6,994,718 B2 | 2/2006 | Groothuis et al. |
| 6,997,939 B2 | 2/2006 | Inder |
| 7,004,954 B1 | 2/2006 | Voss et al. |
| 7,004,955 B2 | 2/2006 | Shen |
| 7,004,956 B2 | 2/2006 | Palmer |
| 7,008,434 B2 | 3/2006 | Kurz et al. |
| 7,033,376 B2 | 4/2006 | Tsukernik |
| 7,041,116 B2 | 5/2006 | Goto |
| 7,048,758 B2 | 5/2006 | Boyle |
| 7,058,456 B2 | 6/2006 | Pierce |
| 7,063,707 B2 | 6/2006 | Bose |
| 7,153,320 B2 | 12/2006 | Euteneuer et al. |
| 7,175,655 B1 | 2/2007 | Malaei |
| 7,179,273 B1 | 2/2007 | Palmer et al. |
| 7,220,269 B1 | 5/2007 | Ansel |
| 7,220,271 B2 | 5/2007 | Clubb |
| 7,226,464 B2 | 6/2007 | Garner et al. |
| 7,229,472 B2 | 6/2007 | DePalma et al. |
| 7,232,462 B2 | 6/2007 | Schaeffer |
| 7,288,112 B2 | 10/2007 | Denardo et al. |
| 7,306,618 B2 | 12/2007 | Demond |
| 7,316,692 B2 | 1/2008 | Huffmaster |
| 7,323,001 B2 | 1/2008 | Cubb |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka |
| 7,556,636 B2 | 7/2009 | Mazzocchi |
| 7,582,111 B2 | 9/2009 | Krolik et al. |
| 7,594,926 B2 | 9/2009 | Linder |
| 7,604,649 B2 | 10/2009 | McGuckin et al. |
| 7,618,434 B2 | 11/2009 | Santra et al. |
| 7,662,165 B2 | 2/2010 | Gilson et al. |
| 7,670,356 B2 | 3/2010 | Mazzocchi |
| 7,691,121 B2 | 4/2010 | Rosenbluth |
| 7,691,124 B2 | 4/2010 | Balgobin |
| 7,708,770 B2 | 5/2010 | Linder |
| 7,736,385 B2 | 6/2010 | Agnew |
| 7,766,934 B2 | 8/2010 | Pal |
| 7,771,452 B2 | 8/2010 | Pal |
| 7,780,694 B2 | 8/2010 | Palmer |
| 7,780,696 B2 | 8/2010 | Daniel et al. |
| 7,819,893 B2 | 10/2010 | Brady et al. |
| 7,828,815 B2 | 11/2010 | Mazzocchi |
| 7,846,176 B2 | 11/2010 | Mazzocchi |
| 7,846,175 B2 | 12/2010 | Bonnette et al. |
| 7,850,708 B2 | 12/2010 | Pal |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi |
| 7,927,349 B2 | 4/2011 | Brady et al. |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | O'Brien et al. |
| 8,052,640 B2 | 11/2011 | Fiorella et al. |
| 8,057,497 B1 | 11/2011 | Raju et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,123,769 B2 | 2/2012 | Osborne |
| 8,137,377 B2 | 3/2012 | Palmer |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,357,178 B2 | 1/2013 | Grandfield et al. |
| 8,357,179 B2 | 1/2013 | Grandfield et al. |
| 8,357,893 B2 | 1/2013 | Xu et al. |
| 8,361,095 B2 | 1/2013 | Osborne |
| 8,366,663 B2 | 2/2013 | Fiorella |
| 8,372,133 B2 | 2/2013 | Douk et al. |
| 8,382,742 B2 | 2/2013 | Hermann et al. |
| 8,409,215 B2 | 4/2013 | Sepetka et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,529,596 B2 | 9/2013 | Grandfield et al. |
| 8,574,262 B2 | 11/2013 | Ferrera et al. |
| 8,579,915 B2 | 11/2013 | French et al. |
| 8,585,643 B2 | 11/2013 | Vo et al. |
| 8,585,713 B2 | 11/2013 | Ferrera et al. |
| 8,608,761 B2 | 12/2013 | Osbourne et al. |
| 8,679,142 B2 | 3/2014 | Slee et al. |
| 8,696,622 B2 | 4/2014 | Fiorella et al. |
| 8,702,652 B2 | 4/2014 | Fiorella et al. |
| 8,702,724 B2 | 4/2014 | Olsen et al. |
| 8,784,434 B2 | 7/2014 | Rosenbluth et al. |
| 8,784,441 B2 | 7/2014 | Rosenbluth et al. |
| 8,795,305 B2 | 8/2014 | Grandfield et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,900,265 B1 | 12/2014 | Ulm, III |
| 8,939,991 B2 | 1/2015 | Krolick et al. |
| 8,945,143 B2 | 2/2015 | Ferrera et al. |
| 8,945,172 B2 | 2/2015 | Ferrera et al. |
| 8,968,330 B2 | 3/2015 | Rosenbluth et al. |
| 9,039,749 B2 | 5/2015 | Shrivastava et al. |
| 9,072,537 B2 | 7/2015 | Grandfield et al. |
| 9,113,936 B2 | 8/2015 | Palmer et al. |
| 9,119,656 B2 | 9/2015 | Bose et al. |
| 9,138,307 B2 | 9/2015 | Valaie |
| 9,149,609 B2 | 10/2015 | Ansel et al. |
| 9,155,552 B2 | 10/2015 | Ulm, III |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,221,132 B2 | 12/2015 | Bowman |
| 9,232,992 B2 | 1/2016 | Heidner |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,635 B2 | 5/2017 | Vale et al. |

(56) References Cited

U.S. PATENT DOCUMENTS

| | | |
|---|---|---|
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 10,028,759 B2 | 7/2018 | Wallace et al. |
| 10,149,692 B2 | 12/2018 | Turjman et al. |
| 10,172,634 B1 | 1/2019 | Horowitz |
| 10,265,086 B2 | 4/2019 | Vale |
| 10,610,668 B2 | 4/2020 | Burkholz et al. |
| 10,716,915 B2 | 7/2020 | Ogle et al. |
| 10,835,271 B2 | 11/2020 | Ma |
| 11,076,879 B2 | 8/2021 | Vale |
| 2001/0001315 A1 | 5/2001 | Bates |
| 2001/0011182 A1 | 8/2001 | Dubrul et al. |
| 2001/0016755 A1 | 8/2001 | Addis |
| 2001/0041899 A1 | 11/2001 | Foster |
| 2001/0044598 A1 | 11/2001 | Parodi |
| 2001/0044634 A1 | 11/2001 | Don Michael et al. |
| 2001/0051810 A1 | 12/2001 | Dubrul |
| 2002/0002383 A1 | 1/2002 | Sepetka et al. |
| 2002/0016609 A1 | 2/2002 | Wensel |
| 2002/0022859 A1 | 2/2002 | Hogendijk |
| 2002/0026211 A1 | 2/2002 | Khosravi |
| 2002/0049468 A1 | 4/2002 | Streeter |
| 2002/0052620 A1 | 5/2002 | Barvut |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0143362 A1 | 10/2002 | Macoviak et al. |
| 2002/0156455 A1 | 10/2002 | Barbut |
| 2002/0161393 A1 | 10/2002 | Demond |
| 2002/0165576 A1 | 11/2002 | Boyle et al. |
| 2002/0173819 A1 | 11/2002 | Leeflang et al. |
| 2002/0177800 A1 | 11/2002 | Bagaoisan et al. |
| 2002/0188276 A1 | 12/2002 | Evans |
| 2003/0004536 A1 | 1/2003 | Boylan et al. |
| 2003/0004538 A1 | 1/2003 | Secrest |
| 2003/0004542 A1 | 1/2003 | Wensel |
| 2003/0009146 A1 | 1/2003 | Muni |
| 2003/0009191 A1 | 1/2003 | Wensel |
| 2003/0023204 A1 | 1/2003 | Vo et al. |
| 2003/0040769 A1 | 2/2003 | Kelley et al. |
| 2003/0040772 A1 | 2/2003 | Hyodoh et al. |
| 2003/0050663 A1 | 3/2003 | Khachin |
| 2003/0100847 A1 | 5/2003 | D'Aquanni et al. |
| 2003/0105484 A1 | 6/2003 | Boyle et al. |
| 2003/0125798 A1 | 7/2003 | Matrin |
| 2003/0130682 A1 | 7/2003 | Broome et al. |
| 2003/0144687 A1 | 7/2003 | Brady et al. |
| 2003/0144689 A1 | 7/2003 | Brady et al. |
| 2003/0153940 A1 | 8/2003 | Nohilly et al. |
| 2003/0153943 A1 | 8/2003 | Michael et al. |
| 2003/0153944 A1 | 8/2003 | Phung |
| 2003/0163064 A1* | 8/2003 | Vrba .................. A61M 25/09 600/585 |
| 2003/0163158 A1 | 8/2003 | Wlite |
| 2003/0171769 A1 | 9/2003 | Barbu |
| 2003/0176884 A1 | 9/2003 | Berrada et al. |
| 2003/0187495 A1 | 10/2003 | Cully et al. |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0212430 A1 | 11/2003 | Bose |
| 2003/0216611 A1 | 11/2003 | Vu |
| 2003/0236533 A1 | 12/2003 | Wilson |
| 2004/0010280 A1 | 1/2004 | Adams et al. |
| 2004/0010282 A1 | 1/2004 | Kusleika |
| 2004/0014002 A1 | 1/2004 | Lundgren |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1 | 4/2004 | Demarais et al. |
| 2004/0093065 A1 | 5/2004 | Yachia et al. |
| 2004/0133231 A1 | 7/2004 | Maitland |
| 2004/0138692 A1 | 7/2004 | Phung |
| 2004/0153049 A1 | 8/2004 | Hewitt et al. |
| 2004/0153118 A1 | 8/2004 | Clubb |
| 2004/0193107 A1 | 9/2004 | Pierpont et al. |
| 2004/0199202 A1 | 10/2004 | Dubrul et al. |
| 2004/0260333 A1 | 12/2004 | Dubrul et al. |
| 2005/0015047 A1 | 1/2005 | Shah |
| 2005/0020974 A1 | 1/2005 | Noriega et al. |
| 2005/0033348 A1 | 2/2005 | Sepetka |
| 2005/0038447 A1 | 2/2005 | Huffmaster |
| 2005/0038468 A1 | 2/2005 | Panetta et al. |
| 2005/0049619 A1 | 3/2005 | Sepetka |
| 2005/0049669 A1 | 3/2005 | Jones |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059993 A1 | 3/2005 | Ramzipoor et al. |
| 2005/0059995 A1 | 3/2005 | Sepetka |
| 2005/0085849 A1 | 4/2005 | Sepetka |
| 2005/0090857 A1 | 4/2005 | Kusleika et al. |
| 2005/0119524 A1 | 6/2005 | Sekine et al. |
| 2005/0119668 A1 | 6/2005 | Teague et al. |
| 2005/0125024 A1 | 6/2005 | Sepetka |
| 2005/0131449 A1 | 6/2005 | Salahieh et al. |
| 2005/0149111 A1 | 7/2005 | Kanazawa et al. |
| 2005/0171566 A1 | 8/2005 | Kanamaru |
| 2005/0187570 A1 | 8/2005 | Nguyen et al. |
| 2005/0267491 A1 | 8/2005 | Kellett et al. |
| 2005/0216030 A1 | 9/2005 | Sepetka |
| 2005/0216050 A1 | 9/2005 | Sepetka |
| 2005/0288686 A1 | 9/2005 | Sepetka |
| 2005/0228417 A1 | 10/2005 | Teitelbaum et al. |
| 2006/0009785 A1 | 1/2006 | Maitland et al. |
| 2006/0009799 A1 | 1/2006 | Kleshinski et al. |
| 2006/0010636 A1 | 1/2006 | Vacher |
| 2006/0030933 A1 | 2/2006 | DeLeggge et al. |
| 2006/0036271 A1 | 2/2006 | Schomer et al. |
| 2006/0058836 A1 | 3/2006 | Bose |
| 2006/0058837 A1 | 3/2006 | Bose |
| 2006/0058838 A1 | 3/2006 | Bose |
| 2006/0064151 A1 | 3/2006 | Guterman et al. |
| 2006/0149313 A1 | 7/2006 | Arguello et al. |
| 2006/0155305 A1 | 7/2006 | Freudenthal |
| 2006/0155322 A1 | 7/2006 | Sater et al. |
| 2006/0161187 A1 | 7/2006 | Levine et al. |

(56) References Cited

U.S. PATENT DOCUMENTS

| | | |
|---|---|---|
| 2006/0195137 A1 | 8/2006 | Sepetka |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0282111 A1 | 12/2006 | Morsi |
| 2006/0287701 A1 | 12/2006 | Pal |
| 2007/0088383 A1 | 4/2007 | Pal et al. |
| 2007/0142858 A1 | 6/2007 | Bates |
| 2007/0149996 A1 | 6/2007 | Coughlin |
| 2007/0156170 A1 | 7/2007 | Hancock |
| 2007/0165170 A1 | 7/2007 | Fukuda |
| 2007/0179513 A1 | 8/2007 | Deutsch |
| 2007/0191866 A1 | 8/2007 | Palmer et al. |
| 2007/0198028 A1 | 8/2007 | Miloslavski |
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |
| 2007/0213765 A1 | 9/2007 | Adams et al. |
| 2007/0225749 A1 | 9/2007 | Martin |
| 2007/0239182 A1 | 10/2007 | Glines et al. |
| 2007/0239254 A1 | 10/2007 | Chia et al. |
| 2007/0244505 A1 | 10/2007 | Gilson et al. |
| 2007/0270902 A1 | 11/2007 | Slazas et al. |
| 2007/0288038 A1 | 12/2007 | Bimbo |
| 2007/0293887 A1 | 12/2007 | Okushi et al. |
| 2008/0045881 A1 | 2/2008 | Teitelbaum et al. |
| 2008/0082107 A1 | 4/2008 | Miller et al. |
| 2008/0086190 A1 | 4/2008 | Ta |
| 2008/0091223 A1 | 4/2008 | Pokorney |
| 2008/0097398 A1 | 4/2008 | Mitelberg et al. |
| 2008/0109031 A1 | 5/2008 | Sepetka |
| 2008/0109032 A1 | 5/2008 | Sepetka |
| 2008/0119886 A1 | 5/2008 | Greenhalgh et al. |
| 2008/0177296 A1 | 7/2008 | Sepetka |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0188928 A1 | 8/2008 | Salahieh et al. |
| 2008/0200946 A1 | 8/2008 | Braun |
| 2008/0215077 A1 | 9/2008 | Sepetka |
| 2008/0221600 A1 | 9/2008 | Dieck et al. |
| 2008/0228209 A1 | 9/2008 | DeMello et al. |
| 2008/0234706 A1 | 9/2008 | Sepetka |
| 2008/0243170 A1 | 10/2008 | Jenson |
| 2008/0255596 A1 | 10/2008 | Jenson |
| 2008/0262528 A1 | 10/2008 | Martin |
| 2008/0262532 A1 | 10/2008 | Martin |
| 2008/0269774 A1 | 10/2008 | Garcia et al. |
| 2008/0275488 A1 | 11/2008 | Fleming |
| 2008/0275493 A1 | 11/2008 | Farmiga |
| 2008/0281350 A1 | 11/2008 | Sepetka |
| 2008/0312681 A1 | 12/2008 | Ansel |
| 2009/0024157 A1 | 1/2009 | Anukhin |
| 2009/0054918 A1 | 2/2009 | Henson |
| 2009/0069828 A1 | 3/2009 | Martin |
| 2009/0076539 A1 | 3/2009 | Valaie |
| 2009/0105722 A1 | 4/2009 | Fulkerson |
| 2009/0105737 A1 | 4/2009 | Fulkerson |
| 2009/0131908 A1 | 5/2009 | McKay |
| 2009/0163846 A1 | 5/2009 | Aklog et al. |
| 2009/0177206 A1 | 7/2009 | Lozier et al. |
| 2009/0182336 A1 | 7/2009 | Brenzel et al. |
| 2009/0221967 A1 | 9/2009 | Thommen et al. |
| 2009/0270815 A1 | 10/2009 | Stamp et al. |
| 2009/0281610 A1 | 11/2009 | Parker |
| 2009/0292297 A1 | 11/2009 | Ferrere |
| 2009/0292307 A1 | 11/2009 | Razack |
| 2009/0299374 A1 | 12/2009 | Tilson et al. |
| 2009/0299393 A1 | 12/2009 | Martin |
| 2009/0306702 A1 | 12/2009 | Miloslavski |
| 2010/0004607 A1 | 1/2010 | Wilson et al. |
| 2010/0016957 A1 | 1/2010 | Jager et al. |
| 2010/0030186 A1 | 2/2010 | Stivland |
| 2010/0030256 A1 | 2/2010 | Dubrul et al. |
| 2010/0036312 A1 | 2/2010 | Krolik et al. |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0137846 A1 | 6/2010 | Desai et al. |
| 2010/0191272 A1 | 7/2010 | Keating |
| 2010/0211094 A1 | 8/2010 | Sargent, Jr. |
| 2010/0249815 A1 | 9/2010 | Jantzen et al. |
| 2010/0268264 A1 | 10/2010 | Bonnett et al. |
| 2010/0268265 A1 | 10/2010 | Krolik et al. |
| 2010/0292726 A1 | 11/2010 | Olsen et al. |
| 2010/0305566 A1 | 12/2010 | Rosenblatt et al. |
| 2010/0305604 A1 | 12/2010 | Pah |
| 2010/0318178 A1 | 12/2010 | Rapaport et al. |
| 2010/0324649 A1 | 12/2010 | Mattsson |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009942 A1 | 1/2011 | Gregorich et al. |
| 2011/0022149 A1 | 1/2011 | Cox et al. |
| 2011/0054514 A1 | 3/2011 | Arcand |
| 2011/0054516 A1 | 3/2011 | Keegan |
| 2011/0060359 A1 | 3/2011 | Hannes |
| 2011/0071432 A1 | 3/2011 | Carrillo, Jr. et al. |
| 2011/0077620 A1 | 3/2011 | deBeer |
| 2011/0098683 A1 | 4/2011 | Wiita et al. |
| 2011/0054504 A1 | 5/2011 | Wolf et al. |
| 2011/0125181 A1 | 5/2011 | Brady et al. |
| 2011/0130756 A1 | 6/2011 | Everson, Jr. et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0196414 A1 | 8/2011 | Porter et al. |
| 2011/0202088 A1 | 8/2011 | Eckhouse et al. |
| 2011/0213290 A1 | 9/2011 | Chin et al. |
| 2011/0213297 A1* | 9/2011 | Aklog .............. A61M 1/3621 604/28 |
| 2011/0213393 A1 | 9/2011 | Aklog et al. |
| 2011/0213403 A1 | 9/2011 | Aboytes |
| 2011/0218564 A1 | 9/2011 | Drasler et al. |
| 2011/0224707 A1 | 9/2011 | Miloslavski et al. |
| 2011/0264132 A1 | 10/2011 | Strauss et al. |
| 2011/0276120 A1 | 11/2011 | Gilson et al. |
| 2011/0319917 A1 | 12/2011 | Ferrera et al. |
| 2012/0041449 A1 | 2/2012 | Eckhouse et al. |
| 2012/0041474 A1 | 2/2012 | Eckhouse et al. |
| 2012/0059356 A1 | 3/2012 | diPama et al. |
| 2012/0089216 A1 | 4/2012 | Rapaport et al. |
| 2012/0101510 A1 | 4/2012 | Lenker et al. |
| 2012/0116351 A1 | 5/2012 | Chomas et al. |
| 2012/0116440 A1 | 5/2012 | Leynov et al. |
| 2012/0143237 A1 | 6/2012 | Cam et al. |
| 2012/0143239 A1 | 6/2012 | Aklog et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2013/0006284 A1 | 1/2013 | Aggerholm et al. |
| 2013/0025934 A1 | 1/2013 | Aimi et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144326 A1 | 6/2013 | Brady et al. |
| 2013/0144328 A1 | 6/2013 | Weber et al. |
| 2013/0158592 A1 | 6/2013 | Porter |
| 2013/0184703 A1 | 7/2013 | Shireman et al. |
| 2013/0184739 A1 | 7/2013 | Brady et al. |
| 2013/0197567 A1 | 8/2013 | Brady et al. |
| 2013/0226146 A1 | 8/2013 | Tekulve |

(56) References Cited

U.S. PATENT DOCUMENTS

| | | |
|---|---|---|
| 2013/0268050 A1 | 10/2013 | Wilson et al. |
| 2013/0281788 A1 | 10/2013 | Garrison |
| 2013/0289697 A1 | 10/2013 | Baker et al. |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0012281 A1 | 1/2014 | Wang et al. |
| 2014/0046359 A1 | 2/2014 | Bowman et al. |
| 2014/0052097 A1 | 2/2014 | Petersen et al. |
| 2014/0081243 A1 | 3/2014 | Zhou et al. |
| 2014/0121672 A1 | 5/2014 | Folk |
| 2014/0128905 A1 | 5/2014 | Molaei |
| 2014/0135812 A1 | 5/2014 | Divino et al. |
| 2014/0180377 A1 | 6/2014 | Bose et al. |
| 2014/0188127 A1 | 7/2014 | Dubrul et al. |
| 2014/0194919 A1 | 7/2014 | Losardo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0257018 A1 | 9/2014 | Farnan |
| 2014/0257362 A1 | 9/2014 | Eldenschink |
| 2014/0276922 A1 | 9/2014 | McLain et al. |
| 2014/0277003 A1 | 9/2014 | Hendrick |
| 2014/0277053 A1 | 9/2014 | Wang et al. |
| 2014/0277079 A1 | 9/2014 | Vale et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0364896 A1 | 12/2014 | Consigny |
| 2014/0371769 A1 | 12/2014 | Vale et al. |
| 2014/0371777 A1* | 12/2014 | Rudakov ............ A61B 17/1214 606/198 |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0080937 A1 | 3/2015 | Davidson |
| 2015/0081003 A1 | 3/2015 | Wainwright et al. |
| 2015/0112376 A1 | 4/2015 | Molaei et al. |
| 2015/0133990 A1 | 5/2015 | Davidson |
| 2015/0142043 A1 | 5/2015 | Furey |
| 2015/0164523 A1 | 6/2015 | Brady et al. |
| 2015/0173782 A1* | 6/2015 | Garrison ............... A61M 29/00 606/127 |
| 2015/0173783 A1 | 6/2015 | Tah et al. |
| 2015/0238314 A1 | 8/2015 | Börtlein et al. |
| 2015/0250497 A1 | 9/2015 | Marks et al. |
| 2015/0257775 A1 | 9/2015 | Gilvarry et al. |
| 2015/0258270 A1 | 9/2015 | Kunis |
| 2015/0290437 A1 | 10/2015 | Rudakov et al. |
| 2015/0297252 A1 | 10/2015 | Miloslavski et al. |
| 2015/0306311 A1 | 10/2015 | Pinchuk et al. |
| 2015/0313617 A1 | 11/2015 | Grandfield et al. |
| 2015/0320431 A1 | 11/2015 | Ulm, III |
| 2015/0351770 A1 | 12/2015 | Fulton, III |
| 2015/0352325 A1 | 12/2015 | Quick |
| 2015/0359547 A1 | 12/2015 | Vale et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0066921 A1 | 3/2016 | Brady et al. |
| 2016/0074067 A1 | 3/2016 | Furnish et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0121080 A1 | 5/2016 | Cottone |
| 2016/0135829 A1 | 5/2016 | Holochwost et al. |
| 2016/0143653 A1 | 5/2016 | Vale et al. |
| 2016/0151079 A1 | 6/2016 | Aklog et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0228134 A1 | 8/2016 | Martin et al. |
| 2016/0256180 A1 | 9/2016 | Vale et al. |
| 2016/0262880 A1 | 9/2016 | Li et al. |
| 2016/0317168 A1 | 11/2016 | Brady et al. |
| 2016/0346002 A1 | 12/2016 | Avneri et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0065401 A1 | 3/2017 | Fearnot et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086864 A1* | 3/2017 | Greenhalgh ..... A61B 17/22031 |
| 2017/0086996 A1 | 3/2017 | Peterson et al. |
| 2017/0095138 A1 | 4/2017 | Nakade et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100142 A1 | 4/2017 | Look et al. |
| 2017/0100143 A1 | 4/2017 | Granfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172554 A1 | 6/2017 | Bortlein et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0238953 A1 | 8/2017 | Yang et al. |
| 2017/0239447 A1* | 8/2017 | Yang .................... A61M 1/743 |
| 2017/0252043 A1 | 9/2017 | Fuller et al. |
| 2017/0252064 A1 | 9/2017 | Staunton |
| 2017/0259042 A1 | 9/2017 | Nguyen et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Sethna |

(56) References Cited

U.S. PATENT DOCUMENTS

| | | |
|---|---|---|
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0008407 A1 | 1/2018 | Maimon et al. |
| 2018/0042623 A1 | 2/2018 | Batiste |
| 2018/0193050 A1 | 7/2018 | Hawkins et al. |
| 2018/0193591 A1 | 7/2018 | Jaroch et al. |
| 2018/0235743 A1 | 8/2018 | Farago et al. |
| 2018/0256177 A1* | 9/2018 | Cooper ............... A61B 17/221 |
| 2018/0303610 A1* | 10/2018 | Anderson ......... A61M 25/0023 |
| 2019/0021755 A1 | 1/2019 | Johnson et al. |
| 2019/0021759 A1 | 1/2019 | Krolik et al. |
| 2019/0029820 A1 | 1/2019 | Zhou et al. |
| 2019/0029825 A1 | 1/2019 | Fitterer et al. |
| 2019/0046219 A1 | 2/2019 | Marchand et al. |
| 2019/0192175 A1 | 6/2019 | Chida et al. |
| 2019/0209206 A1 | 7/2019 | Patel et al. |
| 2019/0216476 A1 | 7/2019 | Barry et al. |
| 2019/0239907 A1 | 8/2019 | Brady et al. |
| 2019/0247627 A1* | 8/2019 | Korkuch ............. A61M 60/857 |
| 2019/0255290 A1 | 8/2019 | Snyder et al. |
| 2019/0269491 A1 | 9/2019 | Jalgaonkar et al. |
| 2019/0274810 A1 | 9/2019 | Phouasalit et al. |
| 2019/0298396 A1 | 10/2019 | Gamba et al. |
| 2019/0365411 A1 | 12/2019 | Avneri et al. |
| 2019/0366049 A1 | 12/2019 | Hannon et al. |
| 2020/0038628 A1 | 2/2020 | Chou et al. |
| 2020/0214859 A1* | 7/2020 | Sherburne ............. A61B 17/00 |
| 2020/0281611 A1 | 9/2020 | Kelly et al. |
| 2020/0353208 A1 | 11/2020 | Merhi et al. |
| 2020/0383698 A1* | 12/2020 | Miao ............. A61B 17/320758 |
| 2021/0085935 A1 | 3/2021 | Fahey et al. |
| 2021/0153883 A1 | 5/2021 | Casey et al. |
| 2021/0153884 A1 | 5/2021 | Casey et al. |
| 2021/0154433 A1 | 5/2021 | Casey et al. |
| 2021/0219821 A1 | 7/2021 | Appling et al. |
| 2022/0117614 A1 | 4/2022 | Salmon et al. |
| 2022/0125450 A1 | 4/2022 | Sirhan et al. |
| 2022/0313426 A1 | 10/2022 | Gifford, III et al. |
| 2023/0054898 A1 | 3/2023 | Gurovich et al. |

FOREIGN PATENT DOCUMENTS

| | | |
|---|---|---|
| CN | 1972728 A | 5/2007 |
| CN | 103071195 A | 5/2013 |
| CN | 104507380 A | 4/2015 |
| CN | 104905873 A | 9/2015 |
| CN | 105007973 A | 10/2015 |
| CN | 105307582 A | 2/2016 |
| CN | 105726163 A | 7/2016 |
| CN | 106232059 A | 12/2016 |
| CN | 113040865 A | 6/2021 |
| DE | 202009001951 U1 | 4/2010 |
| DE | 102009056450 A1 | 6/2011 |
| DE | 102010010849 A1 | 9/2011 |
| DE | 102010014778 A1 | 10/2011 |
| DE | 102010024085 A1 | 12/2011 |
| DE | 102011014586 B3 | 9/2012 |
| DE | 20 2020 107013 U1 | 1/2021 |
| EP | 2301450 A1 | 3/2011 |
| EP | 2628455 A1 | 8/2013 |
| EP | 3302312 A1 | 4/2018 |
| EP | 3335647 A2 | 6/2018 |
| EP | 3 420 978 A1 | 1/2019 |
| EP | 4049704 A2 | 8/2022 |
| GB | 2498349 A | 7/2013 |
| JP | 9-19438 A | 1/1997 |
| WO | WO 93/04722 A2 | 3/1993 |
| WO | WO 94/24926 A1 | 11/1994 |
| WO | WO 97/27808 A1 | 8/1997 |
| WO | WO 97/38631 A1 | 10/1997 |
| WO | WO 99/20335 A1 | 4/1999 |
| WO | WO 99/56801 A2 | 11/1999 |
| WO | WO 99/60933 A1 | 12/1999 |
| WO | WO 01/21077 A1 | 3/2001 |
| WO | WO 02/02162 A2 | 1/2002 |
| WO | WO 02/11627 A2 | 2/2002 |
| WO | WO 02/43616 A2 | 6/2002 |
| WO | WO 02/070061 A1 | 9/2002 |
| WO | WO 02/094111 A2 | 11/2002 |
| WO | WO 03/002006 A1 | 1/2003 |
| WO | WO 03/018085 A2 | 3/2003 |
| WO | WO 03/030751 A1 | 4/2003 |
| WO | WO 03/051448 A2 | 6/2003 |
| WO | WO 2004/028571 A1 | 4/2004 |
| WO | WO 2004/056275 A1 | 7/2004 |
| WO | WO 2005/000130 A1 | 1/2005 |
| WO | WO 2005/027751 A1 | 3/2005 |
| WO | WO 2005/027779 A2 | 3/2005 |
| WO | WO 2006/021407 A2 | 3/2006 |
| WO | WO 2006/031410 A2 | 3/2006 |
| WO | WO 2006/107641 A2 | 10/2006 |
| WO | WO 2006/135823 A2 | 12/2006 |
| WO | WO 2007/054307 A2 | 5/2007 |
| WO | WO 2007/068424 A2 | 6/2007 |
| WO | WO 2008/034615 A2 | 3/2008 |
| WO | WO 2008/051431 A1 | 5/2008 |
| WO | WO 2008/131116 A1 | 10/2008 |
| WO | WO 2009/019664 A1 | 2/2009 |
| WO | WO 2009/031338 A1 | 3/2009 |
| WO | WO 2009/076482 A1 | 6/2009 |
| WO | WO 2009/086482 A2 | 7/2009 |
| WO | WO 2009/103125 A1 | 8/2009 |
| WO | WO 2009/105710 A1 | 8/2009 |
| WO | WO 2010/010545 A1 | 1/2010 |
| WO | WO 2010/046897 A1 | 4/2010 |
| WO | WO 2010/075565 A1 | 7/2010 |
| WO | WO 2010/102307 A1 | 9/2010 |
| WO | WO 2010/146581 A1 | 12/2010 |
| WO | WO 2011/013556 A1 | 2/2011 |
| WO | WO 2011/066961 A1 | 6/2011 |
| WO | WO 2011/082319 A1 | 7/2011 |
| WO | WO 2011/095352 A1 | 8/2011 |
| WO | WO 2011/106426 A1 | 9/2011 |
| WO | WO 2011/110316 A1 | 9/2011 |
| WO | WO 2012/052982 A1 | 4/2012 |
| WO | WO 2012/064726 A1 | 5/2012 |
| WO | WO 2012/081020 A1 | 6/2012 |
| WO | WO 2012/110619 A1 | 8/2012 |
| WO | WO 2012/120490 A2 | 9/2012 |
| WO | WO 2012/156924 A1 | 11/2012 |
| WO | WO 2013/016435 A1 | 1/2013 |
| WO | WO 2013/072777 A2 | 5/2013 |
| WO | WO 2013/105099 A2 | 7/2013 |
| WO | WO 2013/109756 A1 | 7/2013 |
| WO | WO 2014/081892 A1 | 5/2014 |
| WO | WO 2014/139845 A1 | 9/2014 |
| WO | WO 2014/169266 A1 | 10/2014 |
| WO | WO 2014/178198 A1 | 11/2014 |
| WO | WO 2014/188300 A1 | 11/2014 |
| WO | WO 2015/061365 A1 | 4/2015 |
| WO | WO 2015/134625 A1 | 9/2015 |
| WO | WO 2015/179324 A2 | 11/2015 |
| WO | WO 2015/179377 A1 | 11/2015 |
| WO | WO 2015/189354 A1 | 12/2015 |
| WO | WO 2016/010995 A1 | 1/2016 |
| WO | WO 2017/004234 A1 | 1/2017 |

(56) References Cited

FOREIGN PATENT DOCUMENTS

| WO | WO 2017/097616 A1 | 6/2017 |
| WO | WO 2018/178979 A1 | 10/2018 |
| WO | WO 2018/193603 A1 | 10/2018 |
| WO | WO 2019/064306 A1 | 4/2019 |
| WO | WO 2019/079296 A1 | 4/2019 |
| WO | WO 2020/139979 A1 | 7/2020 |
| WO | WO 2021/016213 A1 | 1/2021 |
| WO | WO 2021/162678 A1 | 8/2021 |
| WO | WO 2021/167653 A1 | 8/2021 |
| WO | WO 2022/020366 A2 | 1/2022 |

OTHER PUBLICATIONS

Struffert, T., et al. "Intravenous flat detector CT angiography for non-invasive visualisation of intracranial flow diverter: technical feasibility" Eur Radiol 21:1797-1801 (2011).

* cited by examiner

CATHETER WITH ELECTRICALLY ACTUATED EXPANDABLE MOUTH

FIELD OF INVENTION

The present disclosure generally relates to devices and methods for removing acute blockages from blood vessels during intravascular medical treatments. More specifically, the present disclosure relates to a clot retrieval catheter with an electrically actuated expandable mouth.

BACKGROUND

Clot retrieval catheters and devices are used in mechanical thrombectomy for endovascular intervention, often in cases where patients are suffering from conditions such as acute ischemic stroke (AIS), myocardial infarction (MI), and pulmonary embolism (PE). Accessing remote areas such as the neurovascular bed is challenging with conventional technology, as the target vessels are small in diameter, distant relative to the site of insertion, and are highly tortuous.

The clot itself can complicate procedures by taking on a number of complex morphologies and consistencies, ranging from simple tube-shaped structures which assume the shape of the vessel to long, strand-like arrangements that can span multiple vessels at one time. The age of a clot can also affect its compliance, with older clots tending to be less compressible than fresh clots. Fibrin rich clots also present a challenge in having a sticky nature that can cause a clot to roll along the outer surface of a mechanical thrombectomy device rather than being gripped effectively. Combinations of soft and firm clot regions can also separate during aspiration, with fragmentation leading to distal embolization which can occur in vessels that cannot be reached with currently available devices. Additionally, breaking the bonds adhering the clot to the vessel wall without damaging fragile vessels is a significant challenge.

Conventional clot retrieval catheters, especially those for operating in the neurovascular blood vessels, can suffer from a number of drawbacks. First, the diameters of the catheters themselves must be small enough to be advanced into the vasculature, which is very small in the context of the neurovascular system. The catheter must also be sufficiently flexible to navigate the vasculature and endure high strains, while also having the axial stiffness to offer smooth advancement along the route. Once at the target site, typical objects to be retrieved from the body can be substantially larger in size than the catheter tip, making it more difficult to retrieve objects into the tip. For example, fibrin-rich clots can often be difficult to extract as they can become lodged in the tip of traditional fixed-mouth catheters. This lodging can cause softer portions of the clot to shear away from the firmer regions, leading to distal embolization.

Small diameters and fixed tip sizes can also be less efficient at directing the aspiration necessary to remove blood and thrombus material during the procedure. The aspiration suction must be strong enough such that any fragmentation occurring through the use of a mechanical thrombectomy device or other methods can, at the very least, be held stationary so that fragments cannot migrate and occlude distal vessels. When aspirating with a traditional fixed-mouth catheter, however, a significant portion of the aspiration flow ends up coming from vessel fluid proximal to the tip of the catheter where there is no clot. This significantly reduces aspiration efficiency, lowering the success rate of clot removal.

The disclosed design is aimed at providing an improved aspirating retrieval catheter which addresses the above-stated deficiencies.

SUMMARY

Examples presented herein include devices and methods for removing acute blockages from blood vessels during intravascular medical treatments. More specifically, the present disclosure relates to an electrically actuated clot retrieval catheter system. An example system for retrieving an obstruction in a blood vessel can include a catheter, a metallic region, and two conductive wires. The catheter can have a wall that defines an inner lumen of the catheter. The inner lumen can extend between a proximal hub with an electrical current controller and a distal tip of the catheter. The metallic region can include at least two abutting metals in a coiled configuration, forming a bimetallic coil. The metallic region can be located at or near the distal end of the catheter. At least a first portion of a first metal of the metallic region can make up an outer perimeter of the bimetallic coil and at least a portion of a second metal of the metallic region can make up an inner perimeter of the bimetallic coil. The two conductive wires can extend along a longitudinal axis of the catheter and can be in electrical communication with the electrical current controller and in electrical communication with at least a portion of the metallic region.

At least a portion of the metallic region can be configured to reversibly expand from a tight configuration to an expanded configuration upon electrical current stimulation. The tight configuration can include a first diameter that is smaller than a second diameter of the expanded configuration.

At least a portion of the bimetallic coil can be affixed to the catheter at the distal tip and can be engaged with the two conductive wires. A current applied to at least a portion of the bimetallic coil from the two conductive wires can move the bimetallic coil along a deflection between a first end and a second end of the bimetallic coil to the expanded configuration.

The first metal of the at least two abutting metals of the bimetallic coil can include a first thermal expansion coefficient. The second metal of the at least two abutting metals of the bimetallic coil can include a second thermal expansion coefficient. The first thermal expansion coefficient can be different from the second thermal expansion coefficient.

The first metal can include a thermal expansion coefficient lower than the thermal expansion coefficient of the second metal.

At least part of the metallic region can include a radiopaque region.

At least a portion of the distal tip of the catheter can include an elastic jacket disposed around the bimetallic coil. The elastic jacket can form an elastic region of the catheter and can extend proximally from the distal tip of the catheter beyond the metallic region.

The elastic region can be configured to reversibly expand as the bimetallic coil expands from the tight configuration to the expanded configuration.

The system can further include a current path from the electrical current controller, through the two conductive wires, to at least one of a first end and/or a second end of the bimetallic coil affixed to the catheter, through a majority of a length of the bimetallic coil, and through a return path to the electrical current controller.

At least one of the two conductive wires can be electrically affixed to the first end of the bimetallic coil. A return path can include at least the other of the two conductive wires electrically affixed to the second of the bimetallic coil and extending along the longitudinal axis.

Another example system for retrieving an obstruction in a blood vessel can include a catheter and a bimetallic coil. The catheter can include a distal tip having an elastic region. The bimetallic coil can be positioned within the elastic region at the distal tip of the catheter. At least a portion of a first metal makes up an outer perimeter of the bimetallic coil and at least a portion of a second metal makes up an inner perimeter of the bimetallic coil.

At least a portion of the bimetallic coil can be configured to reversibly expand from a tight configuration to an expanded configuration. The tight configuration can include a first diameter that is smaller than a second diameter of the expanded configuration.

At least a portion of the bimetallic coil can be affixed to the catheter and can be encapsulated by an elastic jacket within the elastic region. The expanded configuration can include a deflection between a first end and a second end of the bimetallic coil.

The first metal of the bimetallic coil can include a first thermal expansion coefficient. The second metal of the bimetallic coil can include a second thermal expansion coefficient. The first thermal expansion coefficient can be distinct from the second thermal expansion coefficient. The first metal of the bimetallic coil can include a thermal expansion coefficient lower than the thermal expansion coefficient of the second metal of the bimetallic coil.

They system for retrieving an obstruction in a blood vessel can further include two conductive wires and a metallic region. The two conductive wires can extend along a longitudinal axis of the catheter. An electrical current controller can be configured to provide a first current to at least one of the two conductive wires. The metallic region of the catheter can be in electrical communication with the two conductive wires. The metallic region can include the bimetallic coil. At least a portion of the metallic region can include a radiopaque region. At least a portion of the metallic region can be configured to reversibly expand from a tight configuration to an expanded configuration upon electrical current stimulation.

An example method of retrieving an occlusive thrombus from a blood vessel of a patient can include attaching, at least a portion, of a bimetallic coil within a distal tip of a catheter, connecting a first end of a conductive wire to a metallic region including the bimetallic coil, and connecting a second end of the conductive wire to an electrical current controller. The bimetallic coil within the metallic region can include a first metal having a first thermal expansion coefficient and a second metal having a second thermal expansion coefficient distinct from the first thermal expansion coefficient. At least a portion of the bimetallic coil can be affixed to the catheter.

The method of retrieving an occlusive thrombus from a blood vessel of a patient can further include applying an electrical current, through the conductive wire, from an electric current controller to a first end of the bimetallic coil. The method can further include expanding, by the electrical current, the bimetallic coil from a tight configuration to an expanded configuration. The method can further include attaching an elastic jacket around the metallic region.

BRIEF DESCRIPTION OF THE DRAWINGS

The above and further aspects of this disclosure are further discussed with the following description of the accompanying drawings, in which like numerals indicate like structural elements and features in various figures. The drawings are not necessarily to scale, emphasis instead being placed upon illustrating principles of the disclosure. The figures depict one or more implementations of the inventive devices, by way of example only, not by way of limitation. It is expected that those of skill in the art can conceive of and combining elements from multiple figures to better suit the needs of the user.

DETAILED DESCRIPTION

Figure 1A:
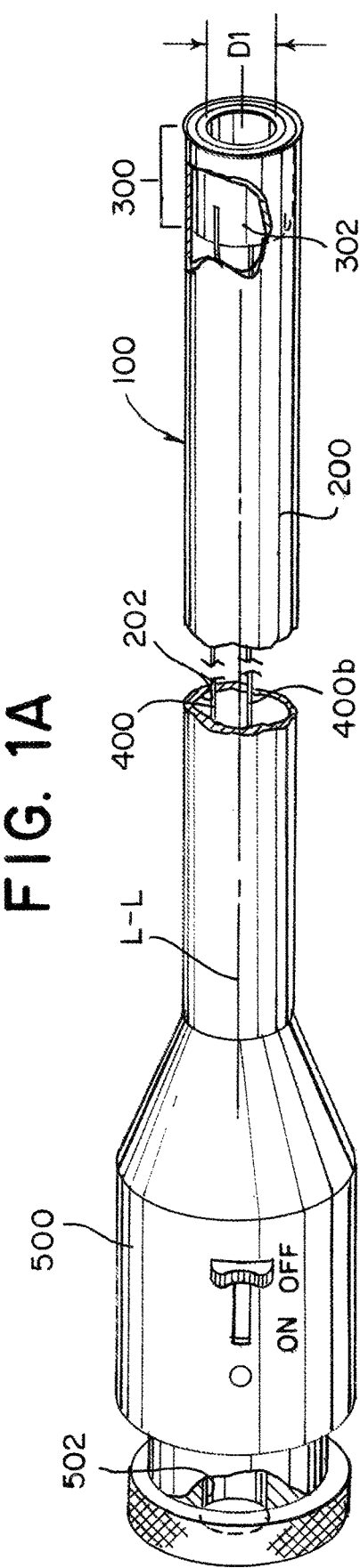
FIGS. 1A and 1B are side-view illustrations of an exemplary actuated clot retrieval system, according to aspects of the present disclosure.

The herein disclosed solution is directed to a clot retrieval catheter capable of expanding to form a funnel to reduce the risk of clot shear and restrict/arrest blood flow via a modular distal tip. Flow restriction and large tipped designs offer substantially greater aspiration efficiency and reduce the risk of emboli migration. Such advantages can also be especially beneficial in the case of stroke intervention procedures, where vessels in the neurovascular bed are particularly small and circuitous, and as a result a clot retrieval catheter with a tip that can expand and decrease can readily move through tortuous vessels while increasing the aspiration efficiency at the clot location. The catheter can also be compatible with relatively low-profile access sheaths and outer catheters, so that a puncture wound in the patient's groin (in the case of femoral access) can be easily and reliably closed. The catheter can also feature internal and/or external low-friction liners, and an outer polymer jacket, elastic sheath, or membrane disposed around the support structure. The membrane can be an elastomeric material that encapsulates the actuated catheter tip having a bimetallic coil at the mouth of the catheter or is fitted over the bimetallic coil so that the mouth of the catheter can move independently of the membrane. The elastomeric membrane can be tight or loose fitting. A loose-fitting elastomeric membrane will be easier to open than a tight-fitting membrane. The membrane can be baggy and made of a non-elastomeric material such that the force to open the membrane is low compared to that of a tight-fitting elastomeric membrane. The membrane can be inverted to extend distally from a proximal location radially inwardly of the mouth of the catheter before reverting back to extend proximally radially outwardly of the mouth of the catheter and wherein the inner and outer layers of the membrane are bonded or reflowed together at a proximal location or for the full length of the membrane. The membrane can comprise an inner and an outer tube, the proximal and distal ends of the inner and outer tube being bonded together or reflowed such that the two tubes form a sock around the catheter tip and bimetallic coil, the bimetallic coil being free to move and expand within the sock.

These improvements can lead to safe and more rapid access of a catheter and other devices to complex areas in order to remove occlusions and shorten procedure times. While the description is in many cases in the context of mechanical thrombectomy treatments, the systems and methods can be adapted for other procedures and in other body passageways as well.

Accessing the various vessels within the vascular system, whether they are coronary, pulmonary, or cerebral, involves well-known procedural steps and the use of a number of conventional, commercially-available accessory products. These products, such as angiographic materials, rotating hemostasis valves, and guidewires are widely used in laboratory and medical procedures. When these products are employed in conjunction with the system and methods in the description below, their function and exact constitution are not known in the related art.

The present systems and methods employ the characteristics of bimetallic materials to customize the distal dimensions of a clot-retrieval device. Bimetallic materials consist of two different metals which can bend or expand at different rates when heated or electrically stimulated. Different thermal expansions allow the bimetallic materials to bend in one direction when heated and in the opposite direction when cooled. Once the heat is removed from the bimetallic material, the material can return to its original position. Alternatively, or in addition thereto, when the heat is removed from the bimetallic material, the clot-retrieval device may be retracted into a guide catheter to assist with returning the bimetallic material to its original position. The bimetallic material can be set to bend or expand to a certain displaced position at a predetermined temperature. Note that while the description discusses bimetallic materials, the invention is not so limited. The inventors contemplate using any alloy that can produce the results described below. This ranges from impurities in a bimetallic alloy to an alloy of three or more elements, metallic or otherwise.

Various examples described herein can include bimetallic materials at the mouth of the catheter such that the mouth of a catheter can resemble a funnel shape once expanded that can exert a radial force on the vasculature. Fluid can be aspirated into the expanded funnel-shaped mouth and then into the catheter to capture a thrombus within the funnel. The bimetallic material can include an elastic jacket covering or membrane that directs the aspirate into the catheter. The bimetallic material can be disposed within an inner lumen of the catheter. As the bimetallic material expands and collapses, the inner diameter of the catheter can be increased and decreased to adjust the flow rate into the catheter.

The present disclosure provides a system for heating a metallic region to cause the bimetallic material to bend into an expanded configuration. One or more conductive wires can provide a current to the metallic region and/or the bimetallic material. The natural electrical conductivity of the bimetallic material can then cause the bimetallic material to bend into an expanded configuration. A thermocouple can also be provided to monitor the temperature of the metallic region and/or the bimetallic material such that the metallic region nor the bimetallic material overheat and cause trauma to the surrounding vasculature. In some examples, a thermoelectric cooling circuit, such as a Peltier chip, can be provided to transition the bimetallic material back into its original position or to bend the opposite direction to cause a tighter configuration of the catheter tip. The present disclosure provides various example designs for bimetallic materials.

Figure 1B:
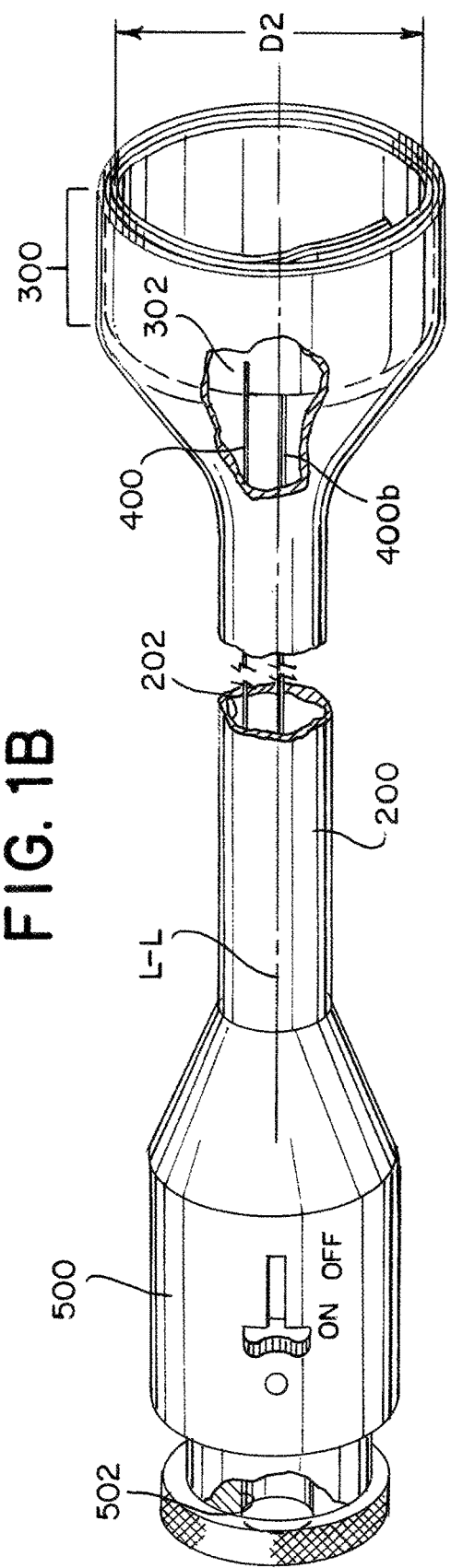

Various devices and methods are disclosed for providing an electrically actuated clot retrieval catheter, and examples of the devices and methods will now be described with reference to the accompanying figures. FIGS. 1A and 1B provide an illustration of an example clot retrieval system 100. The system 100 can include a catheter 200 having a wall that defines an inner lumen 202 of the catheter 200, an electrical current controller 500, and a distal tip. The inner lumen 202 can extend between the proximal hub with an electrical current controller 500 and the distal tip. The system 100 can include a metallic region 300 comprising at least two abutting metals in a coiled configuration, the "bimetallic coil" 302. The bimetallic coil 302 can be positioned at the distal tip of the catheter 200. The bimetallic coil 302 can expand the distal tip of the catheter 200, as shown in FIG. 1B. In some examples, the bimetallic coil 302 can be disposed within the inner lumen 202 of the catheter 200, within the wall of the catheter 200, or within a membrane, as will be described in greater detail below.

The bimetallic coil 302 can be encapsulated within an inverted membrane, dual layer sealed membrane or an overmoulded or dipped membrane, forming an elastic jacket, to be discussed further below. Where the bimetallic coil 302 is housed within an inner and outer membrane layer, the bimetallic coil 302 can have unhindered movement. Where an overmoulded membrane is supplied, there may be more resistance as the bimetallic coil 302 may be required to stretch more discrete areas of membrane material. It is appreciated that, as an electrical current will be passed through the metallic region 300 and/or the bimetallic coil 302, the metallic region 300 and bimetallic coil 302 can be insulated in order to contain the electrical current. The membrane material can serve to insulate the metallic region 300 and the bimetallic coil 302.

The bimetallic coil 302 can have an expanded configuration and a tight configuration. FIG. 1A shows a bimetallic coil 302 in the tight configuration, having a first diameter D1, while FIG. 1B shows the same bimetallic coil 302 in the expanded configuration, having a second diameter D2. In some examples, the expanded configuration can be a shape of a funnel.

The bimetallic coil 302 can include at least two abutting metals. As shown in FIGS. 3A through 3F, at least a portion of a first metal 304 of the metallic region can be positioned on the exterior of the coil shape and form an outer perimeter of the bimetallic coil 302. Similarly, at least a portion of a second metal 306 of the metallic region can be positioned on the interior of the coil shape and form an inner perimeter of the bimetallic coil 302. The different metal materials can be joined together along their length by riveting, brazing, welding, or any other suitable manner to join two metal materials.

The first metal 304 can have a first thermal expansion coefficient. The second metal 306 can have a second thermal expansion coefficient. The first thermal expansion coefficient can be different than the second thermal expansion coefficient, such that the two abutting metals forming the bimetallic coil 302 can transition from a collapsed configuration to an expanded configuration, or vice versa, upon being heated and return to its previous configuration upon cooling. The metal material of the bimetallic coil 302 can include any suitable metal-based materials including, but not limited to steel, copper, and brass. In some examples, the bimetallic coil 302 can include two or more materials that have different coefficients of thermal expansion and can also include radiopaque and/or biocompatible metal-based materials. In one example, the bimetallic coil does not include shape memory material such as Ni—Ti (Nitinol). Alternately, Nitinol, in whole or in part, can be used for the bimetallic coil 302, but its shape memory features are set to temperature generated by the electrical current controller 500 and not body temperature.

Metal-based materials with two or more different coefficients enable devices to be manufactured such that, once heated, the metal material having the lower thermal expansion coefficient can cause the bimetallic coil 302 of the device to bend or expand into an expanded shape. In general, the higher a coefficient of thermal expansion that a material has, the more the material will expand in response to being heated. Considering the example bimetallic coil 302 of FIGS. 1A and 1B, the bimetallic coil 302 can be provided in a collapsed configuration (FIG. 1A). The bimetallic coil 302 can then be heated to a suitable temperature such that the material with a lower thermal expansion coefficient can bend and expand the bimetallic coil 302 and cause the distal tip of the device to form an expanded configuration (FIG. 1B). Once the source of heat is removed, either by removing the electrical current or other methods, the bimetallic coil 302 is re-cooled such that the material having the thermal expansion coefficient causes the bimetallic coil 302 to return to its tight configuration (FIG. 1A). In some examples, the cooling can be achieved easily through conduction with the wires and/or thermocouple wires, and subsequentially through the catheter 200 elastic jacket 204 disposed around the bimetallic coil 302 and/or membrane material. In certain examples, the elasticity of the elastic jacket 204 disposed around the bimetallic coil 302 may assist in causing the bimetallic coil 302 to return to its tight configuration.

Figure 2A:
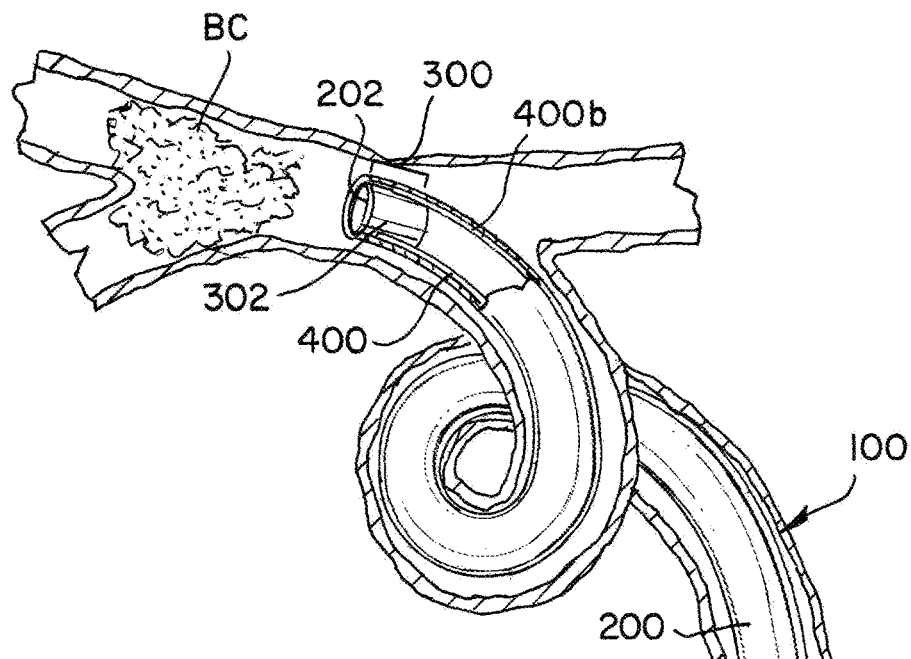
FIGS. 2A and 2B illustrate a method of delivering an exemplary actuated clot retrieval system to a target site within a vessel, according to aspects of the present disclosure.
Figure 2B:
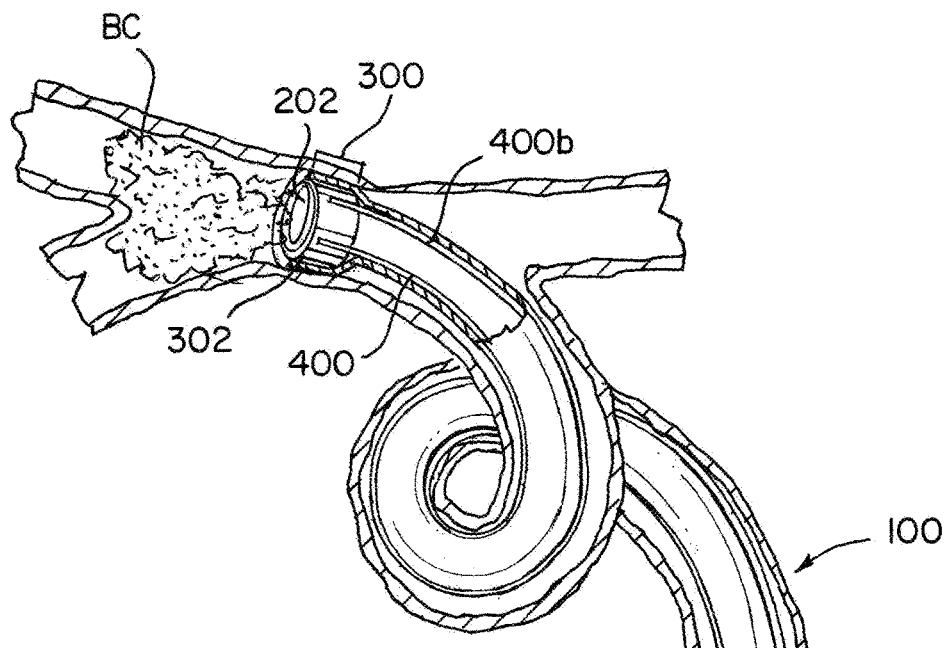
Figure 2B:
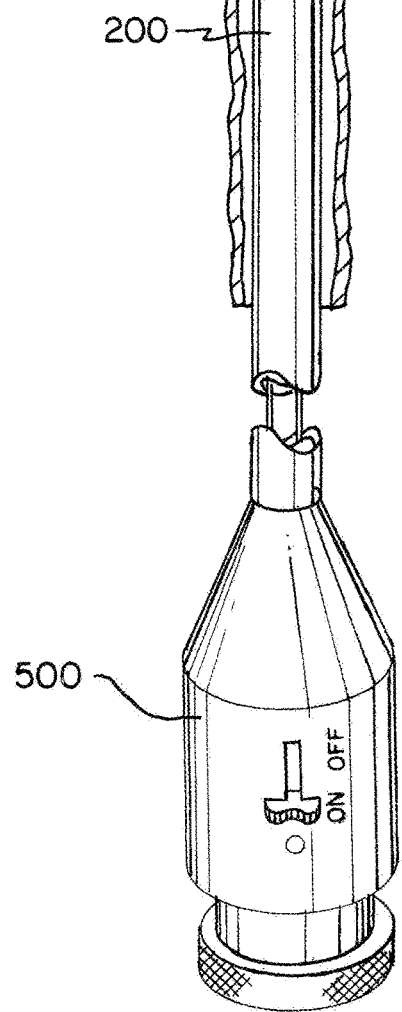
Figure 3A:
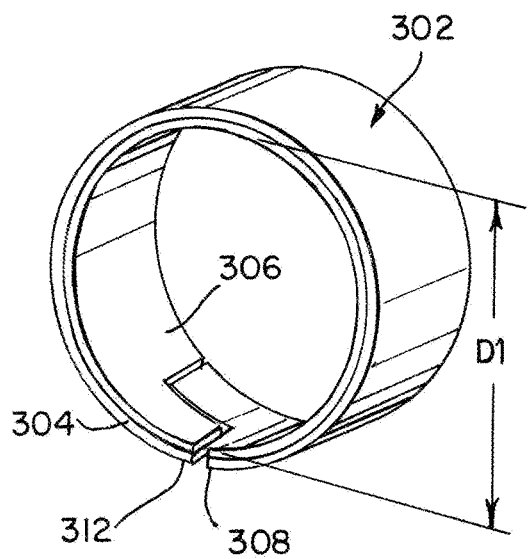
FIGS. 3A through 3F are illustrations of exemplary bimetallic coil designs, according to aspects of the present disclosure.
Figure 3B:
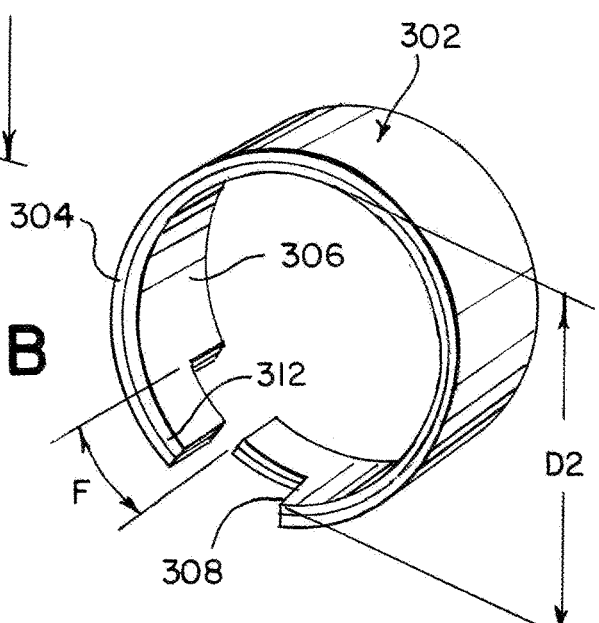
Figure 3C:
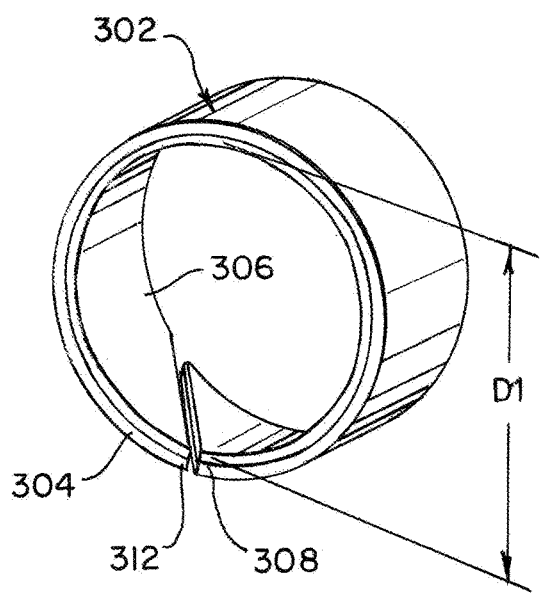
Figure 3D:
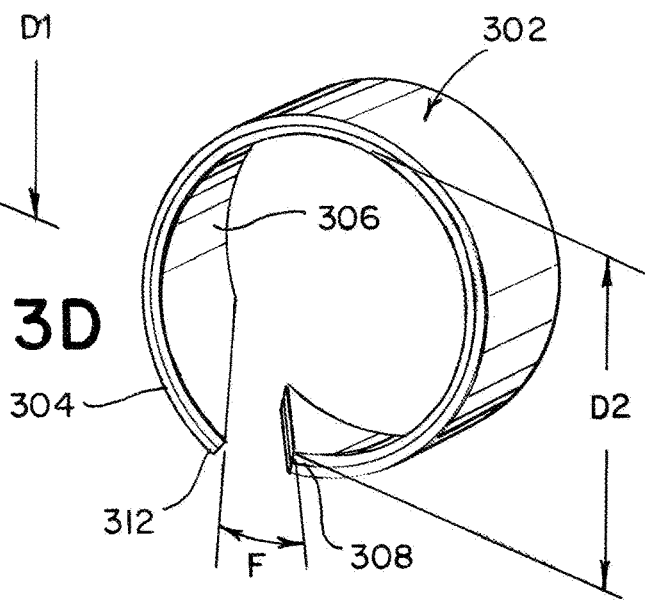
Figure 3E:
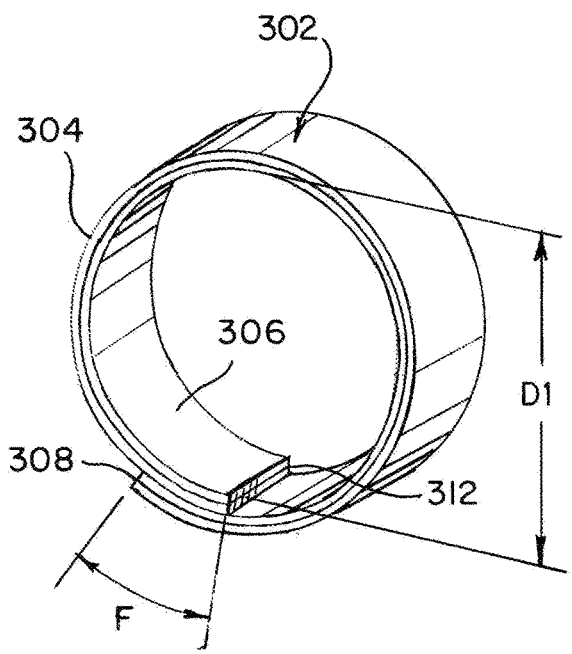
Figure 3F:
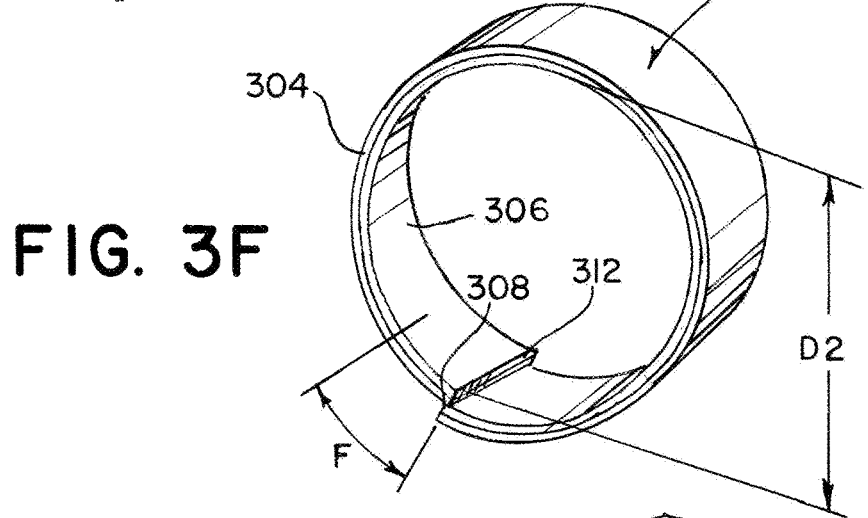

FIGS. 2A and 2B provide an example method of using the transition characteristics of bimetallic materials to actuate a clot retrieval system 100. The actuated clot retrieval system 100 including the catheter 200 and bimetallic coil 302 can be advanced to a target site in a vessel containing a blood clot (BC). This can be completed by advancing the system 100 through an outer catheter. However, as will be described below, the catheter 200 and bimetallic coil 302 can be advanced to the target site without the need for an outer catheter. Once the catheter 200 and bimetallic coil 302 reach the target site, the bimetallic coil 302 can be in its tight configuration, as shown in FIG. 2A. This can enable the bimetallic coil 302 to advance through the tortuous blood vessel with ease. Once the bimetallic coil 302 is at the target site, the bimetallic coil 302 can be heated, which is described in greater detail below, to enable the bimetallic coil 302 to transition from the tight configuration to the expanded configuration. In the example shown in FIG. 2B, when heated, the bimetallic coil 302 expands to a funnel shape that can exert a force on the vessel. The clot can then be aspirated into the catheter through the expanded bimetallic coil 302 and removed from the target site. In some examples, the bimetallic coil 302 can be actively cooled such that the bimetallic coil 302 collapses into its tight configuration to capture the clot. Alternatively, the bimetallic coil 302 can automatically cool when the electrical current is removed from the bimetallic coil 302 and subsequently through the catheter 200 elastic jacket 204 disposed around the bimetallic coil 302 and/or membrane material. In addition, the elastic jacket 204 disposed around the bimetallic coil 302 may assist in causing the bimetallic coil 302 to return to its tight configuration once electrical current is removed from the bimetallic coil 302.

Referring again to FIGS. 1A and 1B, various bimetallic materials, including the alloys described above, have different linear thermal expansion coefficients, enabling the system 100 to be customized for the particular procedure. The bimetallic materials (first metal 304 and/or second metal 306) can be selected or processed such that the thermal expansion coefficients are above human blood (e.g., above 37° C.) so that the bimetallic coil 302 is not inadvertently activated prior to reaching the intended activation location in a vessel. The thermal expansion coefficients of the materials can independently range from about $8 \times 10^{-6}$ m/(m ° C.) to about $20 \times 10^{-6}$ m/(m ° C.), which can correlate to a temperature range between 20° C. and 212° C. (e.g., between 20° C. and 65° C., between 40° C. and 60° C., etc.). Ideally the thermal expansion coefficients can correlate to a temperature range between about 45° C. to about 55° C. This can help ensure expandable properties for a delivery configuration while minimizing the energy required to heat the bimetallic coil 302 for transition from the tight configuration to the expanded configuration.

As used herein, the terms "about" or "approximately" for any numerical values or ranges indicate a suitable dimensional tolerance that allows the part or collection of components to function for its intended purpose. More specifically, "about" or "approximately" may refer to the range of values±10% of the recited value, e.g. "about 50° C." may refer to the range of values from 45.001° C. to 54.999° C.

The bimetallic coil 302 can be heated by providing a current to the bimetallic coil 302. The high electrical conductance of the bimetallic materials, for example steel and copper, can cause the bimetallic coil 302 to heat in response to the electrical current and the heat in turn cause the transition from the tight configuration to the expanded configuration. The system 100 can include a proximal hub with an electronic current controller 500 to provide the required current to the bimetallic coil 302. The electronic current controller 500 can be activated with a switch, such as an on-off switch with electrical contacts that can be connected to an electrical current source. The electronic current controller 500 can include a colored LED bulb, or other suitable indicator. The colored LED bulb can flash when the bimetallic coil 302 is configured to expand in an "on" mode. The electronic current controller 500 can feed from approximately 300 mA to approximately 1500 mA (e.g., approximately 500 mA to approximately 1000 mA) to the bimetallic coil 302 using a power supply ranging, for example, from approximately 3 to 12 V, more preferably from approximately 5 to 9 V. The current can be pulsed from 1 to 1000 msec, more preferable from 100 to 500 msec with a break in current of between 1 and 1000 msec, more preferably from 1 to 100 msec. Pulsing allows the temperature of the bimetallic coil 302 to be maintained between a set temperature range, the on segment of the pulses heating and the off segment of the pulse allowing the bimetallic coil 302 to cool such that the temperature is kept between a range. The temperature can be monitored by a thermocouple such that the pulses can be altered if the temperature goes out of range; for example, a continuous feed of current can be used to ramp up the temperature quickly and the pulses can be lowered to keep the temperature of the bimetallic coil 302 under the upper range. The electronic current controller 500 can also have an opening 502 on the proximal end of the electronic current controller 500 to provide access to the inner lumen 202 of the catheter 200. The opening 502 can be configured to fit a luer connector fitting with luer threads or other suitable connectors. The luer connector can provide access to the inner lumen 202 of the catheter 200. As shown in FIGS. 1A and 1B, the luer connector can include external threads to assist in providing secured access to the inner lumen 202 of the catheter 200.

One or more conductive wires 400, 400b (e.g., a positive lead and a negative lead) can extend between the electronic current controller 500 and the bimetallic coil 302 to provide the electrical current to heat the bimetallic coil 302. The electrical current controller 500 can include an on-off switch with electrical contacts that can be connected to an electrical current source. The conductive wires 400, 400b can be embedded within layers of the catheter 200 so that the wire is not exposed on the outer or inner surface of the catheter 200. This can enable the system 100 to be advanced into an outer catheter without the wire restricting the movement of the system 100 through the outer catheter. The conductive wires 400, 400b can comprise copper or any other material suitable to provide a current to the bimetallic coil 302. Embedded conductive wires 400, 400b throughout the length of the shaft of the catheter 200 can increase the tensile strength and resistance to stretching of the catheter 200 between the electronic current controller 500 and the bimetallic coil 302. Increasing the strength of the shaft of the catheter 200 is desirable during aspiration and can offer greater aspiration efficiency and extraction of clots.

The system 100 can further include a thermocouple connected to the bimetallic coil 302 to monitor the temperature of the bimetallic coil 302. If the bimetallic coil 302 is heated above a certain temperature, the bimetallic coil 302 can burn the surrounding vasculature. To prevent this, the thermocouple can monitor the temperature of the bimetallic coil 302 as it is heated by the current. If the bimetallic coil 302 exceeds a certain temperature, for example 50° C., the thermocouple can communicate this information to the electronic current controller 500 to deactivate the current being supplied to the bimetallic coil 302. The thermocouple can comprise a platinum, stainless-steel, or other suitable conductive wire that can be welded between the bimetallic coil 302 (e.g., at an anchor strut) and one of the two conductive wires 400, 400b, where electronic current controller 500 measures the difference in resistivity between the bimetallic coil 302 and the thermocouple wire to determine the temperature of the bimetallic coil 302. This can be calibrated and can have a linear temperature relationship.

The system 100 can include a thermoelectric cooling circuit in electrical communication with the bimetallic coil 302. The thermoelectric cooling circuit can include, for example, a Peltier chip, disposed proximate the bimetallic coil 302. As described above, when the bimetallic coil 302 is cooled, the metal material of the bimetallic coil having a lower thermal expansion coefficient can bend or transition back into the tight configuration. This can be completed to capture the clot in the bimetallic coil 302. Instead of allowing the bimetallic material to cool naturally, the thermoelectric cooling circuit can pump heat from the bimetallic coil 302 to cool the bimetallic coil 302 more rapidly.

Although not shown, the system 100 can be used in combination with an aspiration source. In many cases the expanded bimetallic coil 302 can seal with the walls of the vessel at the target sit to direct aspiration to the distal end of the catheter 200. In other words, the expanded bimetallic coil 302 can also arrest flow and prevent the unwanted aspiration of blood, or emboli migration proximal to the bimetallic coil 302.

FIGS. 2A and 2B depict the catheter 200 for the bimetallic coil 302 inserted through a blood vessel. In some examples, the catheter 200 may be inserted through an outer catheter, however, the outer catheter is not required. As depicted in FIGS. 2A and 2B, the catheter 200 for the bimetallic coil 302 can be the only catheter required to be advanced from a guide catheter (guide catheter not shown in FIG. 2A or 2B). The catheter 200 and bimetallic coil 302, for example, can travel farther away from a guide catheter because the system is highly flexible and self-actuating. Therefore, the guide catheter can reside in the internal carotid artery, for example, and catheter 200 and bimetallic coil 302 can extend entirely to an M1 or M2 vessel.

FIGS. 3A through 3F are illustrations of exemplary bimetallic coil designs. The bimetallic coil 302 can have a variety of shapes, including an overlapping coil, or a spring coil. Alternatively, the bimetallic coil 302 can have a shape that reduces coil crossing or overlap when in the tight configuration, such as a step interlock coil (FIGS. 3A and 3B), angle interlock coil (FIGS. 3C and 3D), and the like. The length of the bimetallic coil 302 can be longer or shorter than the one shown. The length can be increased, for example, to provide more surface-area contact with the vessel wall or increase the reception space for a clot within the bimetallic coil 302.

The metallic region 300 or the bimetallic coil 302 can be formed primarily of a non-radiopaque material such as steel and can include a radiopaque region 314 made of a radiopaque material such as platinum and/or tungsten. The radiopaque material and the non-radiopaque material of the bimetallic coil 302 can be concentrically welded. The radiopaque region 314 can be positioned within the bimetallic coil 302 or within the metallic region 300 near the bimetallic coil 302. The radiopaque region 314 can be positioned a predetermined distance from a distal tip of the catheter 200 so that a physician can readily visualize the placement of the distal tip, the metallic region 300, or the bimetallic coil 302 of the catheter 200 during a treatment procedure.

Figure 4A:
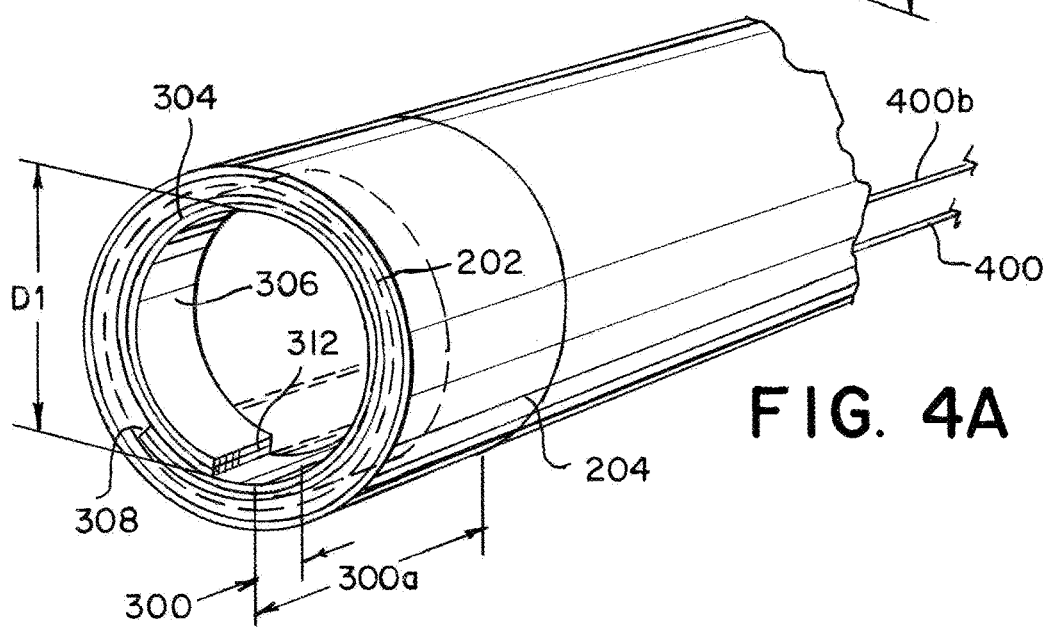
FIGS. 4A and 4B are illustrations of exemplary actuated clot retrieval system having an expandable tip, according to aspects of the present disclosure.
Figure 4B:
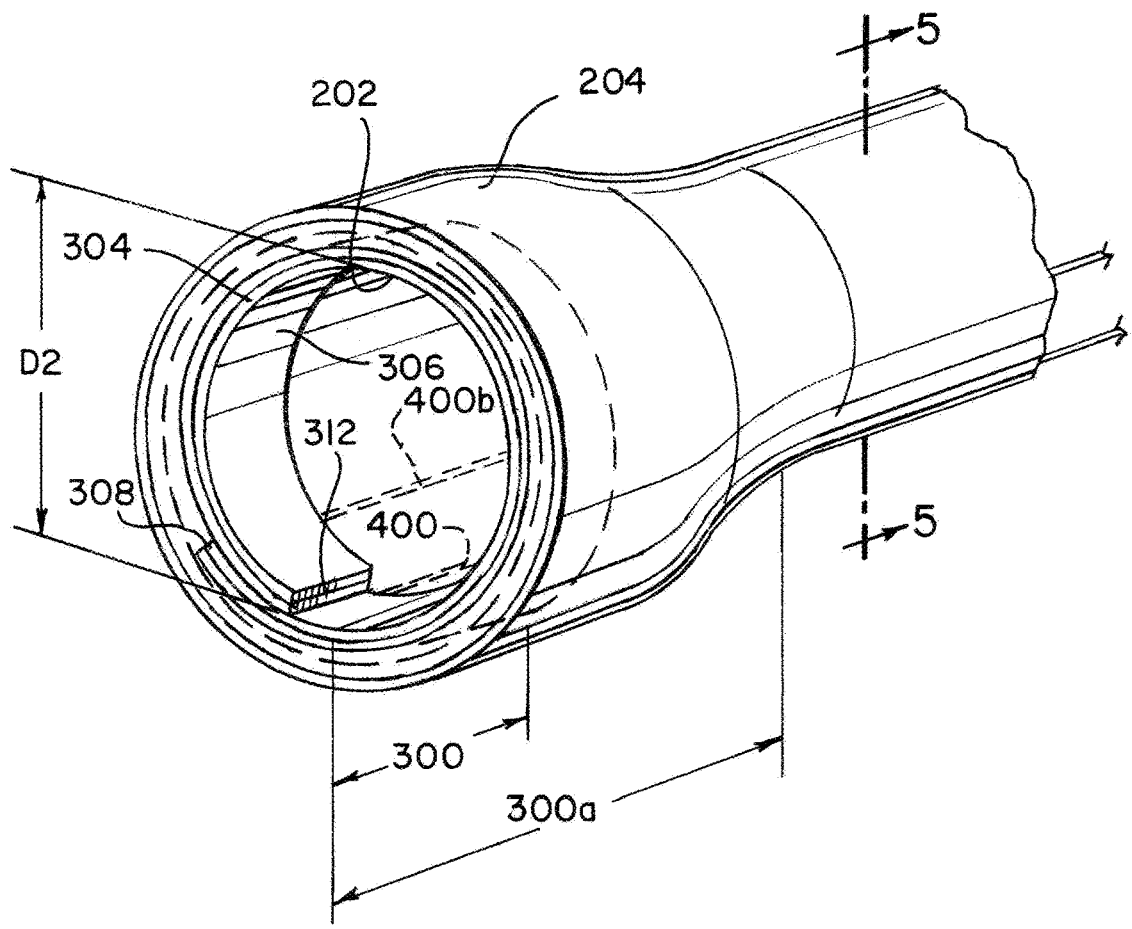

FIGS. 4A and 4B are illustrations of exemplary actuated clot retrieval system having an expandable tip. The catheter tip can have an elastic region 300a that extends proximally from the distal tip of the catheter 200 and over at least a portion of the metallic region 300. In some examples, the elastic region 300a extends over the entire metallic region 300. For example, the metallic region 300 can extend proximally from the distal tip of the catheter 200 and along the longitudinal axis L-L for approximately 1 mm or less, while the elastic region 300a can extend proximally from the distal tip of the catheter 200 and along the longitudinal axis L-L for approximately 1 mm or more. The elastic region 300a can form an atraumatic tip at the distal tip of the catheter 200. The bimetallic coil 302 can be enclosed within an elastic jacket 204. The elastic jacket 204 can provide a means to direct fluid aspirate into the bimetallic coil 302 and into the catheter 200. The elastic jacket 204 can also maintain the position of the bimetallic coil 302 in a collapsed configuration. Elastic jacket 204 materials can include suitable elastic polyurethanes such as Chronoprene, Chronosil, Chronoflex, and other silicon and urethane polymers and the like that have high elasticity and insulative properties with good tear resistance. The elastic jacket 204 can have a low hardness to enable the elastic jacket 204 to stretch when the bimetallic coil 302 is expanded. For example, the elastic jacket 204 can have a Shore hardness typical of 00 ranges and Shore A0.1 to Shore A100 (e.g., Shore A40 to Shore A80). Because the elastic jacket 204 is encapsulating the bimetallic coil 302, which may be intended to expand, the elastic jacket 204 can also have a degree of expandability, for example from 200-2200% (e.g., from 400-800%).

The surface of the bimetallic coil 302 can be coated with a film of material with high dielectric strength such as Parylene to insulate the metal material from blood, which is a conductor, for example if the bimetallic coil 302 is not fully encapsulated or sealed by the elastic jacket 204.

The bimetallic coil 302 can be held in place within the metallic region 300 at the distal tip of the catheter 200 by the elastic jacket 204 described above and by affixing the two conductive wires 400, 400*b*. The two conductive wires 400, 400*b* can be affixed by welding, riveting, brazing, or other suitable methods. In some examples, the two conductive wires 400, 400*b* can be affixed to certain portions of the bimetallic coil 302 such that the first end 308 and the second end 312 of the bimetallic coil 302 can move or bend independently. Alternatively, the first end 308 of the bimetallic coil 302 can be affixed to the catheter 200 such that the first end 308 is fixed and the second end 312 is free to move or bend as the bimetallic coil 302 expands and contracts.

Figure 5:
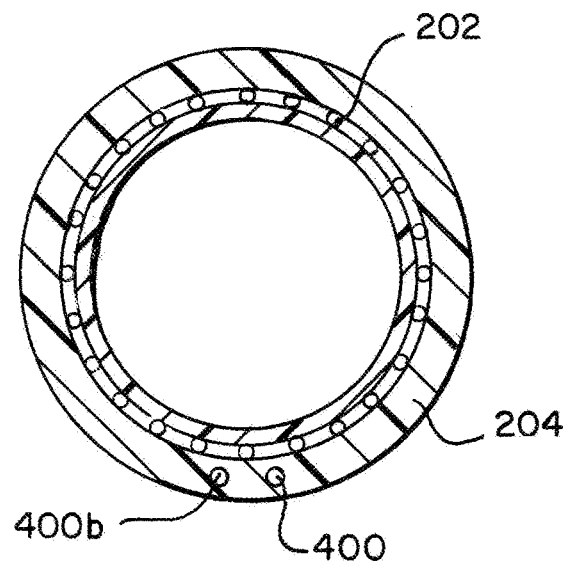
FIG. 5 is a cross-sectional illustration of an exemplary actuated clot retrieval system having embedded conductive wires, according to aspects of the present disclosure.

FIG. 5 is a cross-sectional illustration of an exemplary actuated clot retrieval system having embedded conductive wires. In some examples, insulating certain portions of the bimetallic coil 302 may enable the bimetallic coil 302 to have a distinct activation sequence. The first end 308 of the bimetallic coil 302 can be configured to expand upon receiving current and the second end 312 of the bimetallic coil 302 can be configured to tighten upon receiving current. This can enable the user to tighten or collapse the bimetallic coil 302 by applying a current to one portion of the bimetallic coil 302 instead of waiting for the metal material to cool. Current can flow through a negative lead into one side of a bimetallic coil 302 and flow in an even electrical resistance path to the other side of the bimetallic coil 302 where it returns through a positive lead. Segments of the bimetallic coil 302 can be divided by insulators and different segments can each have independent sets of positive and negative lead wires.

In some examples, instead of extending from the catheter 200, the bimetallic coil 302 can be positioned within an inner lumen 202 of the catheter 200. In a similar manner, as the bimetallic coil 302 expands inside the inner lumen 202, the bore size of the catheter 200 can increase to adjust the flow.

Figure 6:
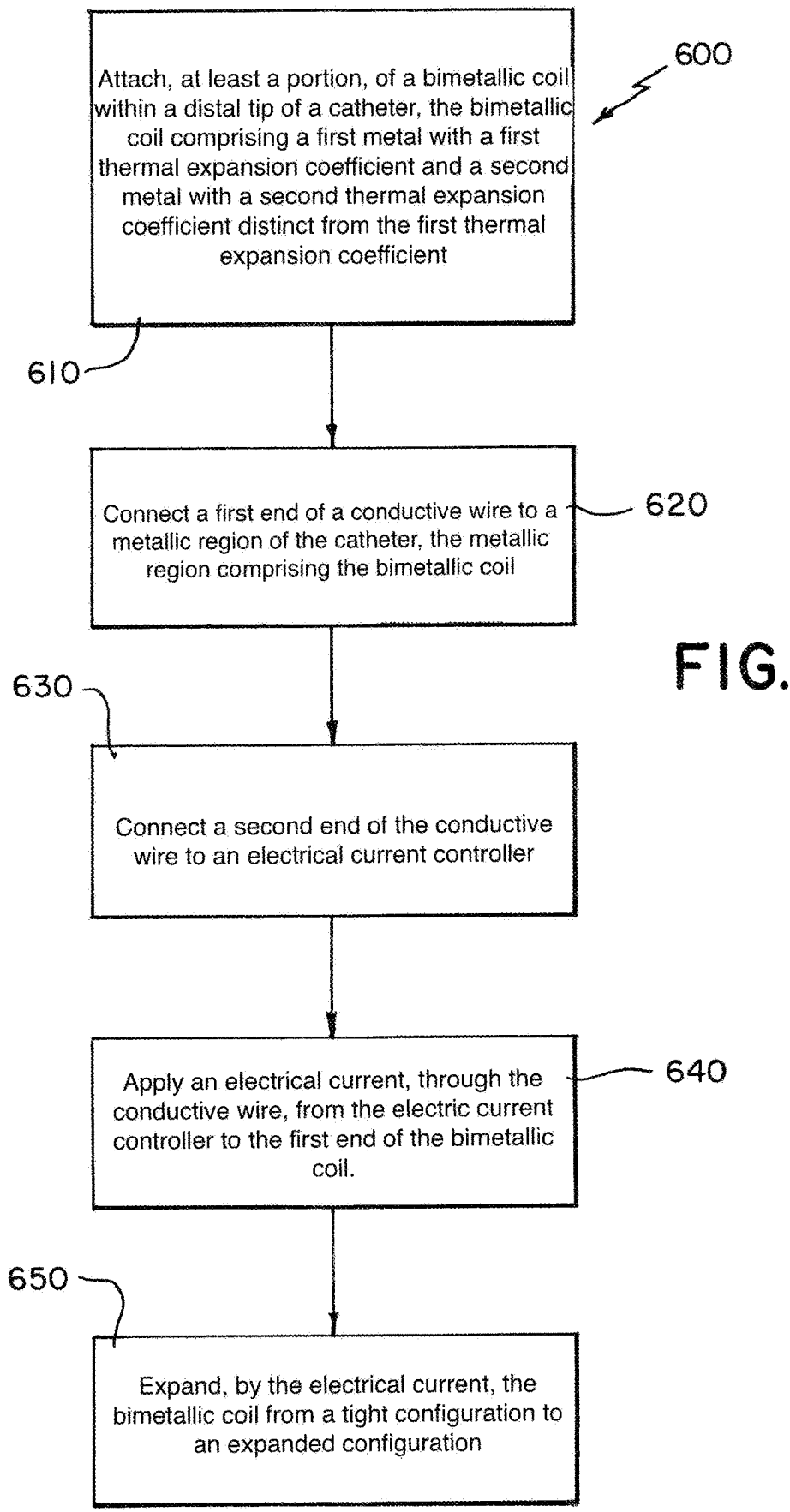
FIG. 6 is a flow diagram illustrating a method of manufacturing a clot retrieval system, according to aspects of the present disclosure.

FIG. 6 is a flow diagram illustrating a method of manufacturing a clot retrieval system. The method steps in FIG. 6 can be implemented by any of the example means described herein or by similar means, as will be appreciated. Referring to method 600 as outlined in FIG. 6, in step 610, method 600 can include attaching at least a portion of a bimetallic coil within a distal tip of a catheter. The bimetallic coil can include a first metal with a first thermal expansion coefficient and a second metal with a second thermal expansion coefficient distinct from the first thermal expansion coefficient.

In step 620, method 600 can include connecting a first end of a conductive wire to a metallic region of the catheter. The metallic region can include the bimetallic coil such that the conductive wire is affixed to the metallic region or affixed directly to the bimetallic coil.

At step 630, method 600 can include connecting a second end of the conductive wire to an electrical current controller.

Step 640 includes applying an electrical current, through the conductive wire, from the electrical current controller to the metallic region. Applying the electrical current to the metallic region may also include applying the electrical current directly or indirectly to the bimetallic coil. The user can activate the electronic circuit outside of the patient.

In step 650, method 600 can include expanding, by the electrical current, the bimetallic coil from a tight configuration to an expanded configuration.

Although not shown, method 600 may further include attaching an elastic jacket around the metallic region such that the elastic jacket allows expansion of the metallic region, as described above.

Method 600 can end after step 650. In other embodiments, additional steps according to the examples described above can be performed. For example, method 600 can include advancing a catheter to a target site through an outer catheter or access sheath. Method 600 can also include deactivating the first current to cool at least a first end of the bimetallic coil. Cooling the bimetallic material can cause the at least a first end to tighten upon the occlusive thrombus to improve the capture the thrombus for removal. Method 600 may further include aspirating the occlusive thrombus into the bimetallic coil. The aspiration can be directed into the catheter by the bimetallic coil. Method 600 can also include withdrawing the catheter with the occlusive thrombus from the patient. With the thrombus captured within the bimetallic coil, the thrombus can be pulled from the vessel of the patient without worry of the thrombus dislodging from the catheter due to poor capture.

In some examples, method 600 can include delivering a second current to at least a second end of the bimetallic coil. The second end can have a different transformation characteristic than the first end, such as a different thermal expansion coefficient. For example, the second end can be configured to bend the opposite direction to cause the bimetallic coil to tighten, which means that, once heated, it can collapse upon the thrombus. Accordingly, method 600 can include heating, via the second current, the second end of the bimetallic coil to cause the second portion of the bimetallic coil to change from an expanded configuration to a collapsed configuration and upon the occlusive thrombus.

Method 600 can also include cooling the at least a first end of the bimetallic coil with a thermoelectric cooling circuit to cause the at least a first end of the bimetallic coil to collapse or tighten upon the occlusive thrombus. A thermoelectric cooling circuit, such as a Peltier chip, can pump heat from a system. Using this effect, the thermoelectric cooling circuit can cause the at least a first end of the bimetallic coil to cool and collapse more rapidly around the occlusive thrombus.

Method 600 can include delivering the current in a series of pulses so as to maintain a steady bimetallic coil temperature, and the electronic circuit can monitor the temperature and adjust the pulse duration and/or length accordingly.

Method 600 can also include monitoring a temperature of the bimetallic coil with a thermocouple. In some examples, the thermocouple can monitor to determine if the bimetallic coil exceeds a certain temperature, for example 50° C., and deactivate the first current if the bimetallic coil exceeds the temperature.

The descriptions contained herein are examples of embodiments of the disclosure and are not intended in any way to limit the scope of the disclosure. As described herein, the disclosure contemplates many variations and modifications of the aspiration device including using alternative geometries of structural elements, combining shapes and structural elements from various example embodiments, using alternative materials, etc. These modifications would be apparent to those having ordinary skill in the art to which this disclosure relates and are intended to be within the scope of the claims which follow.

What is claimed is:

1. A system comprising:
   a catheter having a wall that defines an inner lumen of the catheter, the inner lumen extending between a proximal hub with an electrical current controller, and a distal tip;

a metallic region comprising at least two abutting metals in a coiled configuration positioned at the distal tip of the catheter,
  wherein at least a portion of a first metal of the metallic region comprises an outer perimeter of a bimetallic coil and at least a portion of a second metal of the metallic region comprises an inner perimeter of the bimetallic coil; and
two conductive wires extending along a longitudinal axis of the catheter in electrical communication with the electrical current controller and in electrical communication with at least a portion of the metallic region.

2. The system of claim 1,
wherein at least a portion of the metallic region is configured to reversibly expand from a tight configuration to an expanded configuration upon electrical current stimulation, and
wherein the tight configuration comprises a first diameter that is smaller than a second diameter of the expanded configuration.

3. The system of claim 2,
wherein at least a portion of the bimetallic coil is affixed to the catheter at the distal tip and is engaged with the two conductive wires; and
wherein a current applied to at least a portion of the bimetallic coil from the two conductive wires moves the bimetallic coil along a deflection between a first end and a second end of the bimetallic coil to the expanded configuration.

4. The system of claim 1,
wherein the first metal of the at least two abutting metals of the bimetallic coil comprises a first thermal expansion coefficient,
wherein the second metal of the at least two abutting metals of the bimetallic coil comprises a second thermal expansion coefficient, and
wherein the first thermal expansion coefficient is different from the second thermal expansion coefficient.

5. The system of claim 4,
wherein the first thermal expansion coefficient of the first metal is lower than the second thermal expansion coefficient of the second metal.

6. The system of claim 1,
wherein at least part of the metallic region comprises a radiopaque region.

7. The system of claim 1,
wherein at least a portion of the distal tip of the catheter comprises an elastic jacket disposed around the bimetallic coil, forming an elastic region extending proximally from the distal tip of the catheter beyond the metallic region.

8. The system of claim 7,
wherein the elastic region is configured to reversibly expand as the bimetallic coil expands from the tight configuration to the expanded configuration.

9. The system of claim 1,
further comprising a current path from the electrical current controller, through the two conductive wires, to at least one of a first end and/or a second end of the bimetallic coil affixed to the catheter, through a majority of a length of the bimetallic coil, and through a return path to the electrical current controller.

10. The system of claim 9,
wherein at least one of the two conductive wires is electrically affixed to the first end of the bimetallic coil, and
wherein the return path comprises at least the other of the two conductive wires electrically affixed to the second end of the bimetallic coil and extending along the longitudinal axis.

11. A system comprising:
a catheter having a distal tip comprising an elastic region; and
a bimetallic coil positioned within the elastic region at the distal tip of the catheter; and
wherein at least a portion of a first metal comprises an outer perimeter of the bimetallic coil and at least a portion of a second metal comprises an inner perimeter of the bimetallic coil.

12. The system of claim 11,
wherein at least a portion of the bimetallic coil is configured to reversibly expand from a tight configuration to an expanded configuration, and
wherein the tight configuration comprises a first diameter that is smaller than a second diameter of the expanded configuration.

13. The system of claim 12,
wherein at least a portion of the bimetallic coil is affixed to the catheter and is encapsulated by an elastic jacket within the elastic region; and
wherein the expanded configuration comprises a deflection between a first end and a second end of the bimetallic coil.

14. The system of claim 11,
wherein the first metal of the bimetallic coil comprises a first thermal expansion coefficient,
wherein the second metal of the bimetallic coil comprises a second thermal expansion coefficient, and
wherein the first thermal expansion coefficient is distinct from the second thermal expansion coefficient.

15. The system of claim 14,
wherein the first thermal expansion coefficient of the first metal of the bimetallic coil is lower than the second thermal expansion coefficient of the second metal of the bimetallic coil.

16. The system of claim 11,
further comprising two conductive wires extending along a longitudinal axis of the catheter;
an electrical current controller configured to provide a first current to at least one of the two conductive wires; and
a metallic region of the catheter in electrical communication with the two conductive wires,
wherein the metallic region comprises the bimetallic coil,
wherein at least a portion of the metallic region comprises a radiopaque region, and
wherein at least a portion of the metallic region is configured to reversibly expand from a tight configuration to an expanded configuration upon electrical current stimulation.

* * * * *